US007601691B2

(12) United States Patent
Bridon et al.

(10) Patent No.: US 7,601,691 B2
(45) Date of Patent: Oct. 13, 2009

(54) ANTI-OBESITY AGENTS

(75) Inventors: Dominique P. Bridon, San Francisco, CA (US); Roger Leger, Saint-Lambert (CA); Xicai Huang, Kirkland (CA); Karen Thibaudeau, Rosemere (CA); Martin Robitaille, Granby (CA); Peter G. Milner, Los Altos, CA (US)

(73) Assignee: Conjuchem Biotechnologies Inc., Montreal, Quebec (CA)

( * ) Notice: Subject to any disclaimer, the term of this patent is extended or adjusted under 35 U.S.C. 154(b) by 321 days.

(21) Appl. No.: 11/067,556

(22) Filed: Feb. 25, 2005

(65) Prior Publication Data

US 2005/0176643 A1 Aug. 11, 2005

Related U.S. Application Data

(63) Continuation-in-part of application No. 09/657,276, filed on Sep. 7, 2000, now Pat. No. 6,887,470, application No. 11/067,556, which is a continuation-in-part of application No. 11/040,810, filed on Jan. 21, 2005, which is a continuation of application No. 10/471,348, filed as application No. PCT/CA03/01097 on Jul. 29, 2003, now abandoned, said application No. 11/040,810 is a continuation-in-part of application No. 09/623,548, filed as application No. PCT/US00/13576 on May 17, 2000, now Pat. No. 6,849,714.

(60) Provisional application No. 60/400,199, filed on Jul. 31, 2002, provisional application No. 60/400,413, filed on Jul. 31, 2002, provisional application No. 60/159,783, filed on Oct. 15, 1999, provisional application No. 60/153,406, filed on Sep. 10, 1999, provisional application No. 60/134,406, filed on May 17, 1999.

(51) Int. Cl.
*C07K 14/00* (2006.01)
*A61K 38/00* (2006.01)

(52) U.S. Cl. .......................................... 514/12; 530/300
(58) Field of Classification Search ................. None
See application file for complete search history.

(56) References Cited

U.S. PATENT DOCUMENTS

| | | |
|---|---|---|
| 4,206,199 A | 6/1980 | Fujino et al. |
| 4,251,631 A | 2/1981 | Simon |
| 4,423,034 A | 12/1983 | Nakagawa et al. |
| 4,462,941 A | 7/1984 | Lee et al. |
| 4,859,604 A | 8/1989 | Gould et al. |
| 5,493,007 A | 2/1996 | Burnier et al. |
| 5,580,853 A | 12/1996 | Sytkowski |
| 5,612,034 A | 3/1997 | Pouletty et al. |
| 5,654,276 A | 8/1997 | Barrett et al. |
| 5,837,247 A | 11/1998 | Oppenhelm et al. |
| 5,840,733 A | 11/1998 | Krantz et al. |
| 5,843,440 A | 12/1998 | Pouletty et al. |
| 5,874,408 A | 2/1999 | Nayar |
| 5,876,969 A | 3/1999 | Fleer et al. |
| 5,877,151 A | 3/1999 | Pereira |
| 5,877,204 A | 3/1999 | Davison et al. |
| 5,942,620 A | 8/1999 | Krantz et al. |
| 6,063,761 A | 5/2000 | Jones et al. |
| 6,087,375 A | 7/2000 | Bridon et al. |
| 6,103,233 A | 8/2000 | Pouletty et al. |
| 6,107,489 A | 8/2000 | Krantz et al. |
| 6,165,470 A | 12/2000 | Becquart et al. |
| 6,197,813 B1 | 3/2001 | Hegenauer |
| 6,277,583 B1 | 8/2001 | Krantz et al. |
| 6,277,863 B1 | 8/2001 | Krantz et al. |
| 6,329,336 B1 | 12/2001 | Bridon et al. |
| 6,342,225 B1 | 1/2002 | Jones et al. |
| 6,403,324 B1 | 6/2002 | Krantz et al. |
| 6,437,092 B1 | 8/2002 | Ezrin et al. |
| 6,440,417 B1 | 8/2002 | Thibaudeau et al. |
| 6,500,918 B2 | 12/2002 | Ezrin et al. |
| 6,514,500 B1 | 2/2003 | Bridon et al. |
| 6,593,295 B2 | 7/2003 | Bridon et al. |
| 6,602,981 B2 | 8/2003 | Ezrin et al. |
| 6,610,825 B2 | 8/2003 | Ezrin et al. |
| 6,706,892 B1 | 3/2004 | Ezrin et al. |
| 6,818,611 B1 | 11/2004 | Altman |
| 6,887,470 B1 | 5/2005 | Bridon et al. |
| 7,090,851 B1 | 8/2006 | Boudjellab et al. |
| 7,144,854 B1 | 12/2006 | Beliveau et al. |
| 7,256,253 B2 | 8/2007 | Bridon et al. |
| 7,307,148 B2 | 12/2007 | Bousquet-Gagnon et al. |
| 2002/0018751 A1 | 2/2002 | Bridon et al. |
| 2003/0073630 A1 | 4/2003 | Bridon et al. |
| 2003/0105867 A1 | 6/2003 | Colrain et al. |
| 2003/0108568 A1 | 6/2003 | Bridon et al. |

(Continued)

FOREIGN PATENT DOCUMENTS

DE    DD-252539    12/1987

(Continued)

OTHER PUBLICATIONS

Tatemoto, "Isolation and characterization of peptide YY (PYY), a candidate gut hormone that inhibits pancreatic exocrine secretion", Proc. Natl. Acad. Sci. USA 79: 2514-2518 (1982).*

(Continued)

*Primary Examiner*—Anand U Desai
(74) *Attorney, Agent, or Firm*—Lando & Anastasi, LLP

(57) ABSTRACT

The present invention relates to a compound comprising a PYY peptide or a functional derivative thereof, which is coupled to a reactive group. Such a reactive group is capable of reacting on a blood component so as to form a stable covalent bond therewith. The present invention also relates to a conjugate comprising such a compound which is covalently bonded to a blood component. Moreover, the invention also relates to a method of enhancing, in a patient, the anti-obesity activity of a PYY peptide or functional derivative thereof.

39 Claims, 4 Drawing Sheets

U.S. PATENT DOCUMENTS

| | | | |
|---|---|---|---|
| 2003/0170250 | A1 | 9/2003 | Ezrin et al. |
| 2004/0106589 | A1 | 6/2004 | Webb et al. |
| 2004/0127398 | A1 | 7/2004 | Bridon et al. |
| 2004/0138100 | A1 | 7/2004 | Bridon et al. |
| 2004/0156859 | A1 | 8/2004 | Ezrin et al. |
| 2004/0248782 | A1 | 12/2004 | Bridon et al. |
| 2005/0037974 | A1 | 2/2005 | Krantz et al. |
| 2005/0065075 | A1 | 3/2005 | Erickson et al. |
| 2005/0070475 | A1 | 3/2005 | Bridon et al. |
| 2005/0176643 | A1 | 8/2005 | Bridon et al. |
| 2006/0099571 | A1 | 5/2006 | Altman |

FOREIGN PATENT DOCUMENTS

| | | |
|---|---|---|
| DE | 19936780 | 2/2001 |
| EP | 0602290 | 6/1994 |
| EP | 1234586 | 8/2002 |
| JP | 03502691 | 8/1989 |
| JP | 03178998 | 8/1991 |
| WO | 9201476 | 2/1992 |
| WO | WO-93/25217 | 12/1993 |
| WO | 9422467 | 10/1994 |
| WO | WO-95/00534 | 1/1995 |
| WO | WO-95/10302 | 4/1995 |
| WO | WO-96/06626 | 3/1996 |
| WO | 9614854 | 5/1996 |
| WO | 9629342 | 9/1996 |
| WO | WO-96/26544 | 9/1996 |
| WO | WO-97/25074 | 7/1997 |
| WO | WO-97/29372 | 8/1997 |
| WO | WO-98/00171 | 1/1998 |
| WO | 9820885 | 5/1998 |
| WO | WO-99/24074 | 5/1999 |
| WO | WO-99/24075 | 5/1999 |
| WO | WO-99/24076 | 5/1999 |
| WO | WO-99/24462 | 5/1999 |
| WO | WO-99/48534 | 9/1999 |
| WO | WO-99/48536 | 9/1999 |
| WO | WO-00/69900 | 11/2000 |
| WO | WO-00/76550 | 12/2000 |
| WO | WO-00/76551 | 12/2000 |
| WO | 0117568 | 3/2001 |
| WO | 04011498 | 2/2004 |
| WO | 05099768 | 10/2005 |
| WO | 05103087 | 11/2005 |
| WO | 07049941 | 5/2007 |
| WO | 07071068 | 6/2007 |

OTHER PUBLICATIONS

Schechter et al., "Reversible PEGylation of peptide YY(3-36) prolongs its inhibition of food intake in mice", FEBS Letters 579: 2439-2444 (2005).*

U.S. Appl. No. 09/623,633, filed Sep. 5, 2000, Boudjellab et al.

U.S. Appl. No. 09/623,543, filed Sep. 5, 2000, Beliveau et al.

U.S. Appl. No. 09/657,336, filed Sep. 7, 2000, Boudjellab et al.

U.S. Appl. No. 09/657,431, filed Sep. 7, 2000, Beliveau et al.

U.S. Appl. No. 11/066,697, filed Feb. 25, 2005, Bridon et al.

International Search Report mailed Jan. 27, 2004, for PCT patent application No. PCT/CA03/01097 filed on Jul. 29, 2003, 3 pages.

Akil, Huda et al. (1984) "Endogenous Opioids: Biology and Function," Ann. Rev. Neurosci., 7:223-255.

Breton, Jerome et al. (1995) "Prolonged Half-life in the Circulation of a Chemical Conjugate between a Pro-urokinase Derivative and Human Serum Albumin," Eur. J. Biochem., 231:563-569.

Brunner-La Rocca, Hans Peter et al. (2001) "Therapeutic Benefits of Increasing Natriuretic Peptide Levels," Cardiovascular Research, 51:510-520.

Hirai, Yuko et al. (1979) "A New Mast Cell Degranulating Peptide 'Mastoparan' in the Venom of Vespula Lewisii," Chem. Pharm. Bull., 27(8):1942-1944.

Kapas, Supriya et al. (Oct. 1995) "Cloning and Expression of cDNA Encoding a Rat Adrenomedullin Receptor," J. Biol. Chem., 270(43):25344-25347.

Knusli, Claudio et al. (1992) "Polyethylene Glycol (PEG) Modification of Granulocyte-Macrophage Colony Stimulating Factor (GM-CSF) Enhances Neutroophil Priming Activity but not Colony Stimulating Activity," British Journal of Haematology, 82:654-663.

Leger, Roger et al. (2003) "Synthesis and In Vitro Analysis of Atrial Natriuetic Peptide-Albumin Conjugates," Bioorganic & Medicinal Chemistry Letters, 13:3571-3575.

Mumby, Susanne M. et al. (Jan. 1986) "Antisera of Designed Specificity for Subunits of Guanine Nucleotide-Binding Regulatory Proteins," Proc. Natl. Acad. Sci., 83:265-269.

Oren, Ziv et al. (1998) "Mode of Action of Linear Amphipathic α-Helical Antimicrobial Peptides," Biopolymers (Peptide Science), 47:451-463.

Otteson, Kenneth M. et al (1983) "Comparisons of Peptide Sequences with Deprotection Problems in Fmoc Solid Phase Peptide Synthesis," Proceedings of the 8th American Peptide Symposium, pp. 409-412.

Patrias et al. (1994/1995) "Trimethylaminuria (Fish-Malodor Syndrome) and the Flavin Monoxygenases," Biotech Report pp. 106-107.

Reubi, JC et al. (1982) Endocrinology, 110(3):1049-1051.

Selkoe, Dennis J. (1993) "Physiological Production of the β-Amyloid Protein and the Mechanism of Alzheimer's Disease," TINS, 16(10):403-409.

Smith, Francine G. et al. (1989) "Atrial Natriuretic Factor During Fetal and Postnatal Life: A Review," J. Dev. Physiol., 12:55-62.

Stehle, Gerd et al. (1997) "The Loading Rate Determines Tumor Targeting Properties of Methotrexate-Albumin Conjugates in Rats," Anti-Cancer Drugs, 8:677-685.

Thim, Lars et al. (1998) "Molecules in Focus:CART, a New Anorectic Peptide," Int. J. Biochem. Cell. Biol., 30:1281-1284.

Ito, K. et al. (Dec. 1995) "Preparation of Specific Antiserum of Secretin and its Use in Time-Resolved FluoroImmunoassay," Journal of the Pharmaceutical Society of Japan, abstract.

Singer, M. V. et al. (1981) "Effect of Adding Albumin to Solutions of Secretin on Pancreatic Volume and Bicarbonate Response," Scandinavian Journal of Gastroenterology, abstract.

Davis et al., "Reduction of Immunogenicity and Extension of Circulating Half-Life of Peptides and Proteins," Peptide and Protein Drug Delivery, Lee, V. H. L., ed., Marcel Dekker Inc., NY, NY; 831-864 (1991).

Paige et al., "Prolonged Circulation of Recombinant Human Granulocyte-Colony Stimulating Factor by Covalent Linkage to Albumin Through a Heterobifunctional Polyethylene Glycol," Pharm. Res., 12(12): 1883-1888 (1995).

Poznansky, "Enzyme-Protein Conjugates: New Possibilities for Enzyme Therapy," Pharmac. Ther., 21:53-76 (1983).

Poznansky et al., "Growth Hormone-Albumin Conjugates Reduced Renal Toxicity and Altered Plasma Clearance," FEBS Letters, 239(1):18-22 (1988).

Balasubramaniam A. et al., "Syntheses and Receptor Affinities of Partial Sequences of Peptide YY (PYY)", Pept. Res. 1988 1, 32-5.

Balsubramaniam, A. et al., (2000) "Structure-Activity Studies Including a I(CH2-NH) scan of Peptide YY (PYY) Active Site, PYY(22-36), for Interaction with Rat Intestinal PYY Receptors: Development of Analogues with Potent in Vivo Activity in the Intenstine", J. Med. Chem, 43, 3420-3427.

Batterham, et al. "Gut Hormone PYY3-36 Physiology Inhibits Food Intake," Nature 2002, 418, 650-654.

Decarr et al. "A Long-Acting Selective Neuropeptide Y2 Receptor PEGylated Peptide Agonist Reduces Food Intake in Mice", Bioorganic & Medicinal Chemistry Letter, 17:1916-1919, 2007.

Keire, et al. "Solution Structure of Monomeric Peptide YY Supports the Functional Significance of the PP-Fold", Biochemistry, 2000, 39, 9935-9942.

Kratz, et al., "Probing the Cysteine-34 Position of Endogenous Serum Albumin W ith Thiol-Binding Doxorubicin Derivatives. Improved Efficiency of an Acid-Sensitive Doxorubilin Derivative with Specific Albumin-Binding Properties Compared to that of the Parent Compound." J. Med Chem. 2002, 45, 5523-5533.

Nonaka et al., "Characterization of Blood-Brain Barrier Permeabililty to PYY 3-36, in the Mouse", J. Pharmacol. Exp. Ther. 2003, 306, 948-953.

Tatemoto, "Isolation and Characterization of Peptide YY (PYY), a Candidate Gut Hormone that Inhibits Pancreatic Exocrine Secretion", Proc. Natl. Acad. Sci. USA, 79:2514-2518 (1982).

Schechter et al., "Reversible PEGylation of Peptide YY(3-36) Prolongs its Inhibition of Food Intake in Mice", FEBS Letters 579:2439-2444 (2005).

Vona-Davis L. et al., "Peptide YY Attenuates Transcription Factor Activity in Tumor Neurosis Factor-alpha-induced Pancreatis", J. Am. Coll. Surg., 2004, 199, 87-95.

Chance, William T., et al., "Reduction of Gut Hypoplasia and Cachexia in Tumor-Bearing Rats Maintained on Total Parenteral Nutrition and Treated With Peptide YY and Clenbuterol", Nutrition, vol. 14, No. 6, 1998.

Leger, et al., "DAC™ PYY3-36 Albumin Bioconjugate CJC-1682: A Peripherally Long Lasting PYY Analog Reduces Food Intake in Normal Rats", the Endocrine Society's 87th Annual Meeting.

Kratz, et al., "Albumin Conjugates of the Anticancer Drug Chlorambucil: Synthesis, Characterization, and in Vitro Efficacy", Arch. Pharm. Pharm. Med. Chem., vol. 331, No. 2, pp. 47-53, 1998.

Kratz, et al., "Preparation, Characterization and in Vitro Efficacy of Albumin Conjugates of Doxorubicin", Biol. Pharm. Bull., vol. 21, No. 1, pp. 56-61, 1998.

Cruze et al., "The Y2 receptor mediates Increases in Collateral-Dependent Blood Flow in a Model of Peripheral Arterial Insufficiency", Peptides, 28, pp. 269-280, 2007.

Eberlein et al., "A New Molecular Form of PYY: Structural Characterization of Human PYY (3-36) and PYY (1-36)", Peptides, vol. 10, pp. 797-803, 1989.

Takagi et al., "Enhancement of the Thermostability of Subtilisin E by Introduction of A Disulfide Bond Engineered on the Basis of Structural Comparison with a Thermophilic Serine Protease", J. Biol. Chem., vol. 265, No. 12, pp. 6874-6878, 1990.

Tatemoto et al., "Isolation and Primary Structure of Human Peptide YY", Biochem. Biophys. Res. Commun., vol. 157, pp. 713-717, 1988.

* cited by examiner

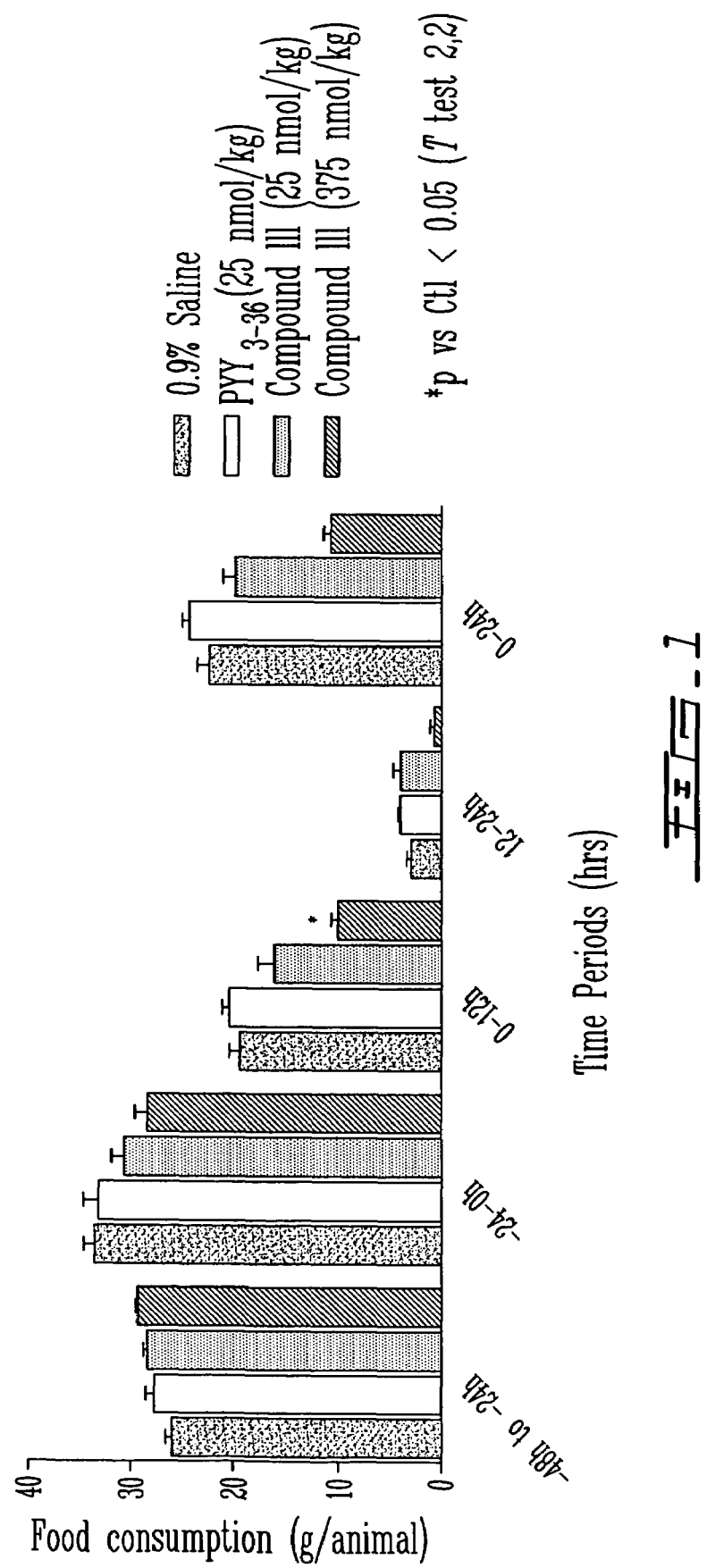

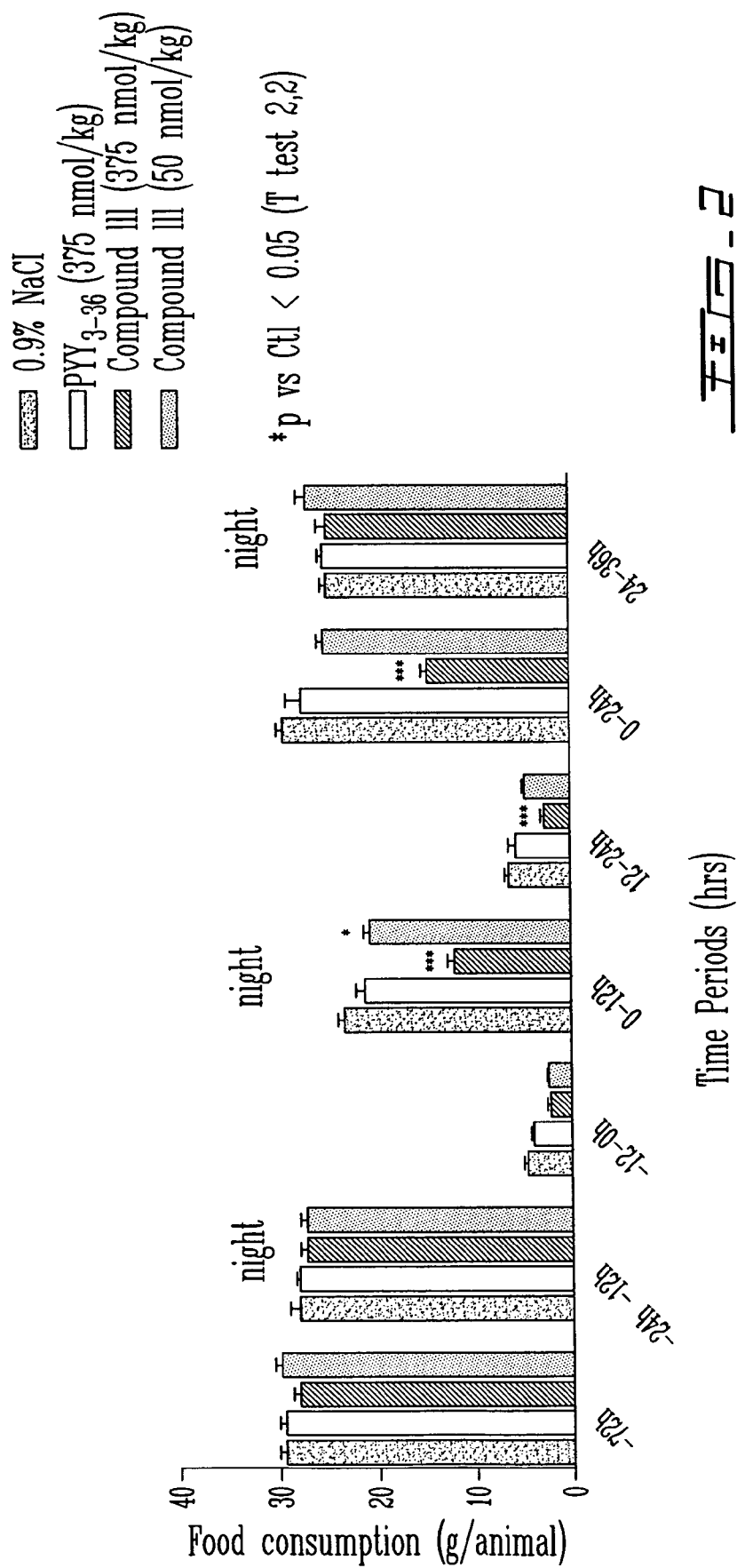

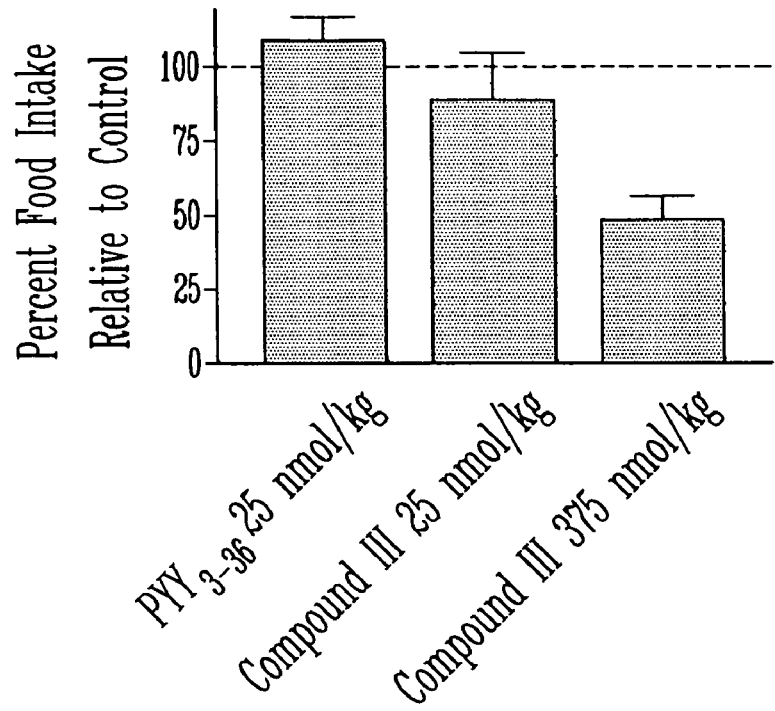
FIG_3
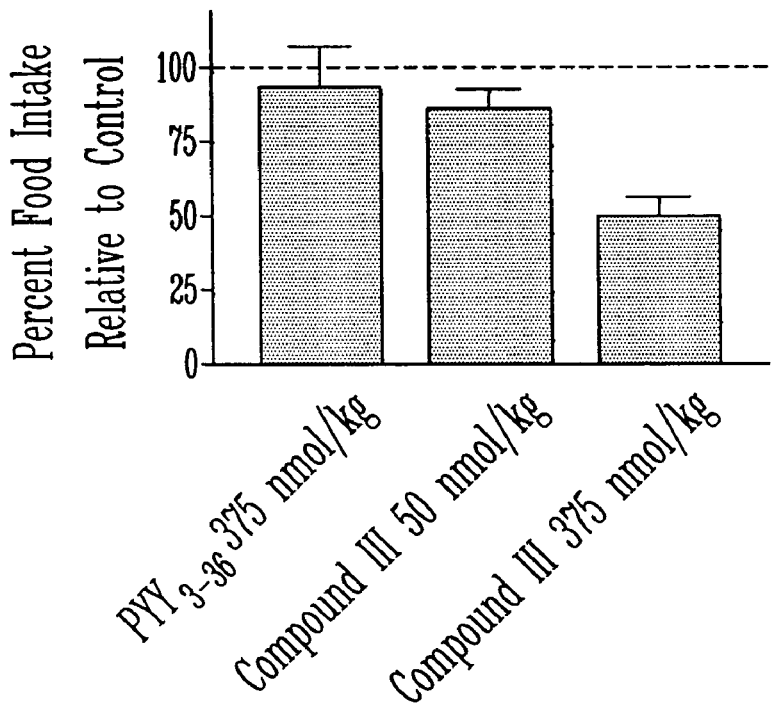
FIG_4

ANTI-OBESITY AGENTS

CROSS-REFERENCE TO RELATED APPLICATIONS

The present application is a Continuation-in-Part of U.S. patent application Ser. No. 09/657,276 filed on Sep. 7, 2000, which claims priority to U.S. Provisional Patent Application No. 60/153,406 filed on Sep. 10, 1999, and to U.S. Provisional Patent Application No. 60/159,783 filed on Oct. 15, 1999. This application is also a Continuation-in-Part Application of U.S. patent application Ser. No. 11/040,810 filed Jan. 21, 2005, which is a Continuation Application of U.S. patent application Ser. No. 10/471,348 filed on Sep. 8, 2003, which is a National Stage of International Patent Application No. PCT/CA03/01097 filed on Jul. 29, 2003, which claims the benefit under 35 U.S.C. §119(e) of U.S. Provisional Patent Application Ser. No. 60/400,199 filed on Jul. 31, 2002, and U.S. Provisional Patent Application Ser. No. 60/400,413 filed on Jul. 31, 2002. U.S. patent application Ser. No. 11/040,810 is also a Continuation-in-Part Application of U.S. patent application Ser. No. 09/623,548 filed on May 17, 2000, now U.S. Pat. No. 6,849,714, which was a National Stage of International Application No. PCT/US00/13576, filed on May 17, 2000, which claims priority to U.S. Provisional Patent Application No. 60/134,406 filed on May 17, 1999, U.S. Provisional Patent Application No. 60/153,406 filed on Sep. 10, 1999, and to U.S. Provisional Patent Application No. 60/159,783 filed on Oct. 15, 1999. The above-mentioned applications are incorporated herein by reference in their entirety.

FIELD OF THE INVENTION

The present invention relates to compounds and methods for treating eating disorders or metabolic syndromes. More particularly, the present relates to peptides, conjugates and methods for treating obesity.

BACKGROUND OF THE INVENTION

A number of postprandial endocrine, paracrine or autocrine messenger products involved in the signaling of hunger and satiety that are present in circulation such as hormones or peptides. The results from an elevated or reduced plasma concentration of one or more of these products will have either global orexigenic or anorexigenic effects.

Examples of peptides associated with anorexigenic effects are pancreatic polyeptide (PP), neuropeptide Y (NPY) and peptide YY (PYY).

These peptides act through Y receptors for which five are known, Y1, Y2, Y3, Y4 and Y5 and regulate pancreatic secretion, gastric emptying and gastric motility. The Y receptors are found throughout the peripheral and central nervous systems as well as on various gastrointestinal organ cells.

Pancreatic polypeptide is secreted in the pancreas and helps control energy homeostasis through inhibition of pancreatic secretions such as for example insulin thus leading to an increased blood glucose level and signaling a need for reduced feeding.

Hypothalamic secreted neuropeptide Y participates in the control of food intake through binding and activation Y1 and possibly Y2 and Y5 receptors.

One of the most discussed examples in recent times is $PYY_{1-36}$. It is produced in endocrine L cells lining the distal small bowel and colon. The prepro PYY is clipped by signal peptidases to give $proPYY_{1-70}$. This peptide is further modified by prohormone dibasic convertase leading to PYY-Gly-Lys-Arg followed by Carboxypeptidase B to give PYY-Gly and finally to $PYY_{1-36}$ by amidation enzyme. It is then released from the cell where a metabolic derivative obtained through DPP-IV cleavage of the two N-terminal amino acids give circulating $PYY_{3-36}$.

$PYY_{1-36}$ binds and activates Y1, Y2 and Y5 receptors found on a variety of cells surfaces as for NPY. The cells are found peripherally in the gastrointestinal tract as well as on the arcuate nucleus. The result of interaction with the Y2 found on the arcuate is thought to lead to a central nervous system response. Alternatively the Y2 receptors found peripherally on the surface of cell within the gastrointestinal tract have been shown to have an effect on gastric motility, gastric acid secretion and intestinal motility. The result of these interactions lead to reduced food and caloric intake.

Unlike $PYY_{1-36}$ which interacts equally with the Y1 and Y2 receptors, $PYY_{3-36}$ is selective to the Y2 receptor. A selective agonist of the Y2 receptor has been demonstrated to be beneficial as compared to a broad agonist. In fact, the Y1 receptor has been associated with hypertension (A. Balasubramaniam et al. *J. Med. Chem.* 2000, 43, 3420-27, Balasubramaniam A et al. *Pept Res.* 1988 1, 32-5). $PYY_{3-36}$ has been demonstrated to reduce food intake in vivo (Nature, 2002, 418, 650-4).

The advantage of using $PYY_{3-36}$ is that it is a natural appetite controlling hormone. There will not psychological side effect from the central nervous system such as when norepinephrine and serotonin reuptake inhibitor or other stimulants are used. Another advantage is that this class of therapeutic agent does not interfere with the absorption of certain nutritional or fat containing elements such as gastrointestinal lipase inhibitor that cause uncomfortable side effects. An inconvenience of using $PYY_{3-36}$ is need for multiple daily administrations.

A new anti-obesity agent that has an enhanced activity and which would permit to avoid the above-mentioned drawbacks would therefore be highly desired. A method for enhancing the anti-obesity activity of a PYY peptide or a functional derivative thereof would also be desired.

SUMMARY OF THE INVENTION

According to one aspect of the invention, there is provided a compound comprising a PYY peptide or a functional derivative thereof which is coupled to a reactive group, the reactive group being capable of reacting with an amino group, a hydroxyl group or a thiol group on a blood component so as to form a stable covalent bond therewith, thereby substantially preventing the PYY peptide or functional derivative thereof from crossing the blood brain barrier.

According to another aspect of the invention, there is provided a conjugate comprising
 a blood component; and
 a PYY peptide or a functional derivative thereof which is coupled to a reactive group, wherein the reactive group is coupled with at least an amino group, a hydroxyl group or a thiol group on the blood component so as to form a stable covalent bond therewith, thereby substantially preventing the PYY peptide or derivative thereof from crossing the blood brain barrier.

It should be understood that, in the compounds and conjugates of the present invention, the stable covalent bond between the PYY peptide or functional derivative thereof and the blood component can be formed in vivo or ex vivo.

According to another aspect of the invention, there is provided a method of enhancing, in a patient, the anti-obesity activity of a PYY peptide or functional derivative thereof comprising the step of covalently bonding the PYY peptide or functional derivative thereof to a blood component, thereby preventing the PYY peptide or functional derivative thereof from crossing the blood brain barrier when administered to the patient, wherein preventing the PYY peptide or functional derivative thereof from crossing the blood brain barrier results in an enhanced anti-obesity activity of the PYY peptide or functional derivative thereof.

According to another aspect of the invention, there is provided in a method for treating obesity by administering a PYY peptide or a functional derivative thereof to a patient, the improvement wherein the PYY peptide or functional derivative thereof is covalently bonded to a blood component so as to prevent the PYY peptide or functional derivative thereof from crossing the blood brain barrier, thereby enhancing its anti-obesity activity.

It should also be understood that, in the methods of the present invention, the covalent bonding between the PYY peptide or the functional derivative thereof and the blood component can be formed in vivo or ex vivo.

According to another aspect of the invention, there is provided a compound comprising a peptide of formula:

$X_1-X_2-X_3-X_4-X_5-X_6-X_7-X_8-X_9-X_{10}-X_{11}-$ (SEQ ID NO: 1)

$X_{12}-X_{13}-X_{14}-X_{15}-X_{16}-X_{17}-X_{18}-X_{19}-X_{20}-$ $X_{21}-X_{22}-X_{23}-X_{24}-X_{25}-X_{26}-X_{27}-X_{28}-X_{29}-$ $X_{30}-X_{31}-X_{32}-X_{33}-X_{34}-X_{35}-X_{36}-A$ wherein
$X_1$ is absent, tyr or ala;
$X_2$ is absent or pro;
$X_3$ is absent, lys or an analog thereof, ile, leu, or ala;
$X_4$ is absent, lys or an analog thereof, or glu;
$X_5$ is absent or pro;
$X_6$ is absent, glu, val or asp;
$X_7$ is absent, ala, tyr or asn;
$X_8$ is absent or pro;
$X_9$ is absent or gly;
$X_{10}$ is absent, glu or asp;
$X_{11}$ is absent, asp or asn;
$X_{12}$ is absent, lys or an analog thereof, or ala;
$X_{13}$ is absent, lys or an analog thereof, ser, thr, or pro;
$X_{14}$ is absent, lys or an analog thereof, ala, or pro;
$X_{15}$ is absent, lys or an analog thereof, or glu;
$X_{16}$ is absent, glu, gln or asp;
$X_{17}$ is absent, leu or met;
$X_{18}$ is absent, lys or an analog thereof, ser, ala, or asn;
$X_{19}$ is absent, arg or gln;
$X_{20}$ is absent or tyr;
$X_{21}$ is absent, tyr or ala;
$X_{22}$ is ala or ser;
$X_{23}$ is ser, asp or ala;
$X_{24}$ is leu;
$X_{25}$ is arg or lys;
$X_{26}$ is his, arg or lys;
$X_{27}$ is tyr;
$X_{28}$ is leu or ile;
$X_{29}$ is asn
$X_{30}$ is leu or met;
$X_{31}$ is val, leu or ile;
$X_{32}$ is thr;
$X_{33}$ is arg or lys;
$X_{34}$ is gln or pro;
$X_{35}$ is arg or lys;
$X_{36}$ is tyr or a derivative thereof; and
A is absent lys or a derivative thereof, and
at least one reactive group coupled to any one of $X_1$ to $X_{36}$ and A, directly or via a linking group.

According to another aspect of the invention, there is provided a conjugate comprising a blood component and a compound having a peptide of formula:

$X_1-X_2-X_3-X_4-X_5-X_6-X_7-X_8-X_9-X_{10}-X_{11}-$ (SEQ ID NO: 1)

$X_{12}-X_{13}-X_{14}-X_{15}-X_{16}-X_{17}-X_{18}-X_{19}-X_{20}-$ $X_{21}-X_{22}-X_{23}-X_{24}-X_{25}-X_{26}-X_{27}-X_{28}-X_{29}-$ $X_{30}-X_{31}-X_{32}-X_{33}-X_{34}-X_{35}-X_{36}-A$ wherein $X_1-X_{36}$ and A are as previously defined, and a reactive group coupled to any one of $X_1-X_{36}$ and A, directly or via a linking group, and wherein the reactive group is coupled with at least an amino group, a hydroxyl group or a thiol group on the blood component so as to form a stable covalent bond therewith.

It has been found that the compounds and conjugates of the present invention demonstrated an enhanced anti-obesity activity with respect to PYY peptides such as $PYY_{1-36}$ and $PYY_{3-36}$. It also has been found that these compounds and conjugates are efficient for reducing the food consumption of a subject, thereby treating or preventing obesity.

It has been found that the methods of the present invention are effective for enhancing the anti-obesity activity of PYY peptide or a derivative thereof and/or for treating obesity. It also has been found that by preventing the compounds or conjugates from crossing the blood brain barrier, an enhanced anti-obesity activity of the PYY peptides or derivative thereof was observed.

The expression "a PYY peptide or a functional derivative thereof" as used herein refers to a PYY peptide such as $PYY_{1-36}$ or $PYY_{3-36}$ or to a functional derivative of the PYY peptide. Such a functional derivative would be understood by a person skilled in the art as a derivative which substantially maintains the activity of the PYY peptide. Preferably, such a functional derivative has an in vitro NPY Y2 receptor binding activity which is at least 1/100 of the in vitro NPY Y2 receptor binding activity of $PYY_{3-36}$. More preferably, the functional derivative has an in vitro NPY Y2 receptor binding activity which is equal or superior to the in vitro NPY Y2 receptor binding activity of $PYY_{3-36}$. In a non-limitative manner, the functional derivative can comprise a peptide of the following formula: $X_1-X_2-X_3-X_4-X_5-X_6-X_7-X_8-X_9-X_{10}-X_{11}-X_{12}-X_{13}-X_{14}-X_{15}-X_{16}-X_{17}-X_{18}-X_{19}-X_{20}-X_{21}-X_{22}-X_{23}-X_{24}-X_{25}-X_{26}-X_{27}-X_{28}-X_{29}-X_{30}-X_{31}-X_{32}-X_{33}-X_{34}-X_{35}-X_{36}-A$ (SEQ ID NO: 1) or $Z_1-Z_2-Z_3-Z_4-Z_5-Z_6-Z_7-Z_8-Z_9-Z_{10}-Z_{11}-Z_{12}$ (SEQ ID NO: 2) wherein $X_1$ to $X_{36}$, and A are as previously defined, and wherein $Z_1$ is ala, $Z_4$ is arg, $Z_8$ is asn, $Z_{12}$ is arg, and $Z_2$, $Z_3$, $Z_5$ to $Z_7$ and $Z_9$ to $Z_{11}$ are selected from the group consisting of the natural amino acids.

The expression "lys or an analog thereof" refers to a lysine or an analog thereof that will substantially maintains the activity of the peptide. In a non-limitative manner, the lys analog can be of formula:

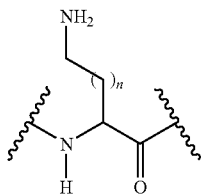

where n is an integer having a value of 0, 1, 2, 3 or 4.

The expression "tyr or a derivative thereof" refers to a tyrosine or a derivative thereof that will substantially maintains the activity of the peptide. In a non-limitative manner, the tyr derivative can be of formula:

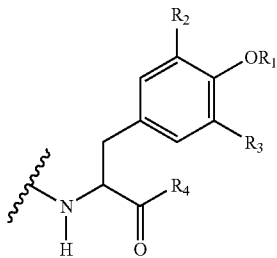

where
$R_1$ is H, a protecting group (PG), a $C_1$-$C_{10}$ branched, linear or cyclic alkyl, a phosphate or a sulfate; $R_2$ and $R_3$ are same or different and selected from the group consisting of H, D and I; and $R_4$ is OH, OPG, $OR_5$, SH, SPG, $SR_5$, $NH_2$, NHPG, $N(PG)_2$, $N(R_5)_2$, $NR_5PG$, or $NHR_6$, where $R_5$ is a $C_1$-$C_{10}$ branched, linear or cyclic alkyl, and $R_6$ is a solid phase support.

The expression "protecting group (PG)" as used herein refers to suitable protecting groups as defined in T. W. Greene and P. G. M. Wuts, Protective Groups in Organic Synthesis, 3rd Edition, (1999) John Wiley & Sons, which is hereby incorporated by reference. The person skilled in the art will understand that nature of the protecting group will vary according to the functionality that has to be protected. Greene et al. discloses, as example, various protecting groups for carboxylic acids, alcohols, thiols, amines, amides etc.

The expression "lys or a derivative thereof" refers to a lysine or a derivative thereof that will substantially maintains the activity of the peptide. In a non-limitative manner, the lys derivative can be of formula:

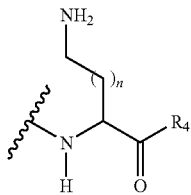

where
$R_4$ is OH, OPG, $OR_5$, SH, SPG, $SR_5$, $NH_2$, NHPG, $N(PG)_2$, $N(R_5)_2$, $NR_5PG$, or $NHR_6$, where $R_5$ is a $C_1$-$C_{10}$ branched, linear or cyclic alkyl, and $R_6$ is a solid phase support; and n is an integer having a value of 0, 1, 2, 3 or 4.

The PYY peptide or functional derivative thereof can be selected from SEQ IDS NO: 1 to 15, preferably from SEQ IDS NO: 2 to 13, and more preferably from SEQ ID NO: 4.

In the compounds and conjugates of present invention, there is preferably only one reactive group. Advantageously, the reactive group is coupled to any one of $X_1$ to $X_{21}$, $X_{23}$, $X_{24}$, $X_{26}$ to $X_{28}$, $X_{30}$ to $X_{32}$, $X_{34}$ to $X_{36}$, and A. Alternatively, the reactive group can be coupled to any one of $Z_1$ to $Z_{12}$ and preferably to any one of $Z_2$, $Z_3$, $Z_5$ to $Z_7$ and $Z_9$ to $Z_{11}$. The reactive group can also be connected to the peptide or the PYY functional derivative by means of a linking group.

According to preferred embodiments, in the compounds and conjugates of the invention which comprise a peptide of formula: $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$-A (SEQ ID NO: 1):

$X_1$ can be absent, the reactive group, linking group-(reactive group), tyr or ala, the tyr or ala being optionally coupled to the reactive group or to the linking group-(reactive group). Preferably, $X_1$ is absent. $X_2$ can be absent, pro, the reactive group or the linking group-(reactive group). Preferably, $X_2$ is absent. $X_3$ can be absent, lys or an analog thereof, (reactive group)-lys, (reactive group)-linking group-lys, (reactive group)-lys analog, (reactive group)-linking group-lys analog, ile, leu, or ala, wherein the reactive group is coupled to the free amine of lys or lys analog. Preferably, $X_3$ is leu. $X_4$ can be absent, lys or an analog thereof, (reactive group)-lys, (reactive group)-linking group-lys, (reactive group)-lys analog, (reactive group)-linking group-lys analog, or glu, wherein the reactive group is coupled to the free amine of lys or lys analog. Preferably, $X_4$ is lys (reactive group)-lys or (reactive group)-linking group-lys. $X_5$ is preferably pro. $X_6$ is preferably glu. $X_7$ is preferably ala. $X_8$ is preferably pro. $X_9$ is preferably gly. $X_{10}$ is preferably glu. $X_{11}$ is preferably asp. $X_{12}$ can be absent, lys or an analog thereof, (reactive group)-lys, (reactive group)-linking group-lys, (reactive group)-lys analog, (reactive group)-linking group-lys analog, or ala, wherein the reactive group is coupled to the free amine of lys or lys analog. Preferably, $X_{12}$ is ala. $X_{13}$ can be absent, lys or an analog thereof, (reactive group)-lys, (reactive group)-linking group-lys, (reactive group)-lys analog, (reactive group)-linking group-lys analog, ser, thr, or pro, wherein the reactive group is coupled to the free amine of lys or lys analog. Preferably, $X_{13}$ is ser. $X_{14}$ can be absent, lys or an analog thereof, (reactive group)-lys, (reactive group)-linking group-lys, (reactive group)-lys analog, (reactive group)-linking group-lys analog, ala or pro, wherein the reactive group is coupled to the free amine of lys or lys analog. $X_{14}$ is preferably pro. $X_{15}$ can be absent, lys or an analog thereof, (reactive group)-lys, (reactive group)-linking group-lys, (reactive group)-lys analog, (reactive group)-linking group-lys analog, or glu, wherein the reactive group is coupled to the free amine of lys or lys analog. $X_{15}$ is preferably glu. $X_{16}$ is preferably glu. $X_{17}$ is preferably leu. $X_{18}$ can be absent, lys or an analog thereof, (reactive group)-lys, (reactive group)-linking group-lys, (reactive group)-lys analog, (reactive group)-linking group-lys analog, ser, ala, or asn, wherein the reactive group is coupled to the free amine of lys or lys analog. $X_{18}$ is preferably asn. $X_{19}$ is preferably arg. $X_{20}$ is preferably tyr. $X_{21}$ can be absent, tyr, ala, a reactive group, or linking group-(reactive group), wherein the linking group is coupled to $X_{20}$ and $X_{22}$. $X_{21}$ is preferably tyr. $X_{22}$ is preferably ala. $X_{23}$ is preferably ser. $X_{25}$ is preferably arg. $X_{26}$ is preferably his.

$X_{28}$ is preferably leu. $X_{30}$ is preferably leu. $X_{31}$ is preferably val. $X_{33}$ is preferably arg. $X_{34}$ is preferably gln. $X_{35}$ is preferably arg.

In a preferred embodiment of the present invention, the reactive group can be selected from the group consisting of Michael acceptors (preferably an unsaturated carbonyl such as a vinyl carbonyl or a vinyl sulfone moiety), succinimidyl-containing groups (such as, N-hydroxysuccinimide (NHS), N-hydroxy-sulfosuccinimide (sulfo-NHS) etc.), an electrophilic thiol acceptor (such as pyridyldithio (Pyr-S—S), an alpha halogenated alkyl carbonyl (such as an alpha halogenated alkyl carbonyl where the alkyl, further to the halogen substituent, may contains or not a substituent such as a $C_1$-$C_8$ alkyl or phenyl), and maleimido-containing groups (such as gamma-maleimide-butyralamide (GMBA), beta-maleimidopropionic acid (MPA), alpha-maleimidoacetic acid (MAA) etc.). Advantageously, the reactive group is a maleimido-containing group. Alternatively, the reactive group is advantageously an alpha halogenated alkyl carbonyl and preferably alpha iodo acetyl. Preferably, the reactive group is a reactive group, which is capable of reacting with an amino group, a hydroxyl group or a thiol group on a blood component so as to form a stable covalent bond.

As example, the maleimido group is most selective for sulfhydryl groups on peptides when the pH of the reaction mixture is kept between 6.5 and 7.4. At pH 7.0, the rate of reaction of maleimido groups with sulfhydryls is 1000-fold faster than with amines. A stable thioether linkage between the maleimido group and the sulfhydryl is formed which cannot be cleaved under physiological conditions. Primary amines can be the principal targets for NHS esters. Accessible α-amine groups present on the N-termini of proteins can react with NHS esters. However, α-amino groups on a protein may not be desirable or available for the NHS coupling. While five amino acids have nitrogen in their side chains, only the ε-amine of lysine reacts significantly with NHS esters. An amide bond can be formed when the NHS ester conjugation reaction reacts with primary amines releasing N-hydroxysuccinimide.

In a preferred embodiment of the present invention, the reactive group is coupled to an amino acid of the peptide via a linking group (or linker), such as, but not limited to (2-amino) ethoxy acetic acid (AEA), ethylenediamine (EDA), amino ethoxy ethoxy succinimic acid (AEES), AEES-AEES, 2-[2-(2-amino)ethoxy)] ethoxy acetic acid (AEEA), AEEA-AEEA, —$NH_2$—$(CH_2)_n$—COOH where n is an integer between 1 and 20 and alkyl chain ($C_1$-$C_{10}$) motif saturated or unsaturated in which could be incorporated oxygen nitrogen or sulfur atoms, such as, but not limited to glycine, 3-aminopropionic acid (APA), 8-aminooctanoic acid (OA) and 4-aminobenzoic acid (APhA) and combinations thereof.

In a preferred embodiment of the present invention, the blood component is a blood protein, more preferably is albumin (such as human serum albumin (HSA)).

Preferably, the invention relates to anti-obesity agents such as $PYY_{3-36}$ or derivatives thereof, which can be shortened versions of the latter. The new bioconjugates formed by the ex vivo, in vivo or in vitro covalent bonding between the peptides of the present invention and a blood component have been found to be very selective to the neuropeptide Y2 receptor.

PP and NPY peptides could also be suitable as an alternative to PYY or its functional derivatives in the various embodiments of the present invention.

The methods of the present invention include extending the effective therapeutic life of the conjugated anti-obesity peptide derivatives as compared to administration of the unconjugated peptide to a patient. Moreover, the anti-obesity activity of the conjugated anti-obesity peptide derivatives of the present invention is considerably enhanced as compared the unconjugated peptide to a patient peptides of the present invention. The derivatives or modified peptides can be of a type designated as a DAC™ (Drug Affinity Complex), which comprises the anti-obesity peptide molecule and a linking group together with a chemically reactive group capable of reaction with a reactive functionality of a mobile blood protein. By reaction with the blood component or protein the modified peptide, or DAC, may be delivered via the blood to appropriate sites or receptors. Moreover, conjugating the peptides to a blood component provides a protection against the degradation of enzymes.

A. Specific Labeling.

Preferably, the compounds, derivatives or modified peptides of this invention are designed to specifically react with thiol groups on mobile blood proteins. Such a reaction is preferably established by covalent bonding of the peptide modified with a maleimido-containing group linked to a thiol group on a mobile blood protein such as serum albumin or IgG.

Under certain circumstances, specific labeling with maleimido-containing group offers several advantages over non-specific labeling of mobile proteins with groups such as NHS and sulfo-NHS. Thiol groups are less abundant in vivo than amino groups. Therefore, the compounds of the present invention such as maleimido-modified peptides, can covalently bond to fewer proteins. For example, in albumin (an abundant blood protein) there is only a single thiol group. Thus, peptide-(maleimido-containing group)-albumin conjugates can tend to comprise a 1:1 molar ratio of peptide to albumin. In addition to albumin, IgG molecules (class II) also have free thiols. Since IgG molecules and serum albumin make up the majority of the soluble protein in blood they also make up the majority of the free thiol groups in blood that are available to covalently bond to maleimide-modified peptides.

Further, even among free thiol-containing blood proteins, including IgGs, specific labeling with a maleimido-containing group leads to the preferential formation of peptide-(maleimido-containing group)-albumin conjugates, due to the unique characteristics of albumin itself. The single free thiol group of albumin, highly conserved among species, is located at amino acid residue 34 (Cys34). It has been demonstrated recently that the Cys34 of albumin has increased reactivity relative to free thiols on other free thiol-containing proteins. This is due in part to the very low pK value of 5.5 for the Cys34 of albumin. This is much lower than typical pK values for cysteine residues in general, which are typically about 8. Due to this low pK, under normal physiological conditions Cys34 of albumin is predominantly in the anionic form, which dramatically increases its reactivity. In addition to the low pK value of Cys34, another factor, which enhances the reactivity of Cys34 is its location in a crevice close to the surface of one loop of region V of albumin. This location makes Cys34 very available to ligands of all kinds, and is an important factor in Cys34's biological role as a free radical trap and a free thiol scavenger. These properties make Cys34 highly reactive toward maleimide-peptides, and the reaction rate acceleration can be as much as 1000-fold relative to rates of reaction of maleimide-peptides with other free-thiol containing proteins.

Another advantage of peptide-(maleimido-containing group)-albumin conjugates is the reproducibility associated with the 1:1 loading of peptide to albumin specifically at Cys34. Other techniques, such as glutaraldehyde, DCC, EDC and other chemical activations of, e.g, free amines, lack this selectivity. For example, albumin contains 52 lysine residues, 25 to 30 of which are located on the surface of albumin and therefore accessible for conjugation. Activating these lysine residues, or alternatively modifying peptides to couple through these lysine residues, results in a heterogenous population of conjugates. Even if statistical 1:1 molar ratios of peptide to albumin are employed, the yield will consist of multiple conjugation products, some containing 0, 1, 2 or more peptides per albumin, and each having peptides randomly coupled at any one or more of the 25 to 30 available lysine sites. Given the numerous possible combinations, characterization of the exact composition and nature of each conjugate batch becomes difficult, and batch-to-batch reproducibility is all but impossible, making such conjugates less desirable as a therapeutic. Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al., "The Loading Rate Determines Tumor Targeting properties of Methotrexate-Albumin Conjugates in Rats," Anti-Cancer Drugs, Vol. 8, pp. 677-685 (1988), the authors report that a 1:1 ratio of the anti-cancer methotrexate to albumin conjugated via amide coupling of one of the available carboxylic acids on methotrexate to any lysine on albumin gave the most promising results. The conjugates describe therein were preferentially taken up by tumor cells, whereas the conjugates bearing 5:1 to 20:1 methotrexate molecules to albumin had altered HPLC profiles and were quickly taken up by the liver in vivo. It is postulated that at these higher ratios, confer conformational changes to albumin diminishing its effectiveness as a therapeutic carrier.

Through controlled administration of maleimido-peptides in vivo, one can control the specific labeling of albumin and IgG in vivo. In typical administrations, 80-90% of the administered maleimido-peptides will label albumin and less than 5% will label IgG. Trace labeling of free thiols such as glutathione, cysteine or Cys-Gly will also occur. Such specific labeling is preferred for in vivo use as it permits an accurate calculation of the estimated half-life of the administered agent.

In addition to providing controlled specific in vivo labeling, maleimide-peptides can provide specific labeling of serum albumin and IgG ex vivo. Such ex vivo labeling involves the addition of maleimide-peptides to blood, serum or saline solution containing serum albumin and/or IgG. Once conjugation has occurred ex vivo with the maleimido-peptides, the blood, serum or saline solution can be readministered to the patient's blood for in vivo treatment.

In contrast to NHS-peptides, maleimido-peptides are generally quite stable in the presence of aqueous solutions and in the presence of free amines. Since maleimido-peptides will only react with free thiols, protective groups are generally not necessary to prevent the maleimido-peptides from reacting with itself. In addition, the increased stability of the modified peptide permits the use of further purification steps such as HPLC to prepare highly purified products suitable for in vivo use. Lastly, the increased chemical stability provides a product with a longer shelf life.

B. Non-Specific Labeling.

The anti-obesity peptides of the invention may also be modified for non-specific labeling of blood components. Bonds to amino groups will also be employed, particularly with the formation of amide bonds for non-specific labeling. To form such bonds, one may use as a chemically reactive group a wide variety of active carboxyl groups, particularly esters, where the hydroxyl moiety is physiologically acceptable at the levels required. While a number of different hydroxyl groups may be employed in these linking agents, the most convenient would be N-hydroxysuccinimide (NHS) and N-hydroxy-sulfosuccinimide (sulfo-NHS).

Other linking agents that may be utilized are described in U.S. Pat. No. 5,612,034, which is hereby incorporated by reference. The various sites with which the chemically reactive group of the modified peptides may react in vivo include cells, particularly red blood cells (erythrocytes) and platelets, and proteins, such as immunoglobulins, including IgG and IgM, serum albumin, ferritin, steroid binding proteins, transferrin, thyroxin binding protein, $\alpha$-2-macroglobulin, and the like. Those receptors with which the modified peptides react, which are not long-lived, will generally be eliminated from the human host within about three days. The proteins indicated above (including the proteins of the cells) will remain at least three days, and may remain five days or more (usually not exceeding 60 days, more usually not exceeding 30 days) particularly as to the half life, based on the concentration in the blood.

For the most part, reaction can be with mobile components in the blood, particularly blood proteins and cells, more particularly blood proteins and erythrocytes. By "mobile" is intended that the component does not have a fixed situs for any extended period of time, generally not exceeding 5 minutes, more usually one minute, although some of the blood component may be relatively stationary for extended periods of time.

Initially, there will be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

The desired conjugates of non-specific modified peptides to blood components may be prepared in vivo by administration of the modified peptides to the patient, which may be a human or other mammal. The administration may be done in the form of a bolus or introduced slowly over time by infusion using metered flow or the like.

If desired, the subject conjugates may also be prepared ex vivo by combining blood with modified peptides of the present invention, allowing covalent bonding of the modified peptides to reactive functionalities on blood components and then returning or administering the conjugated blood to the host. Moreover, the above may also be accomplished by first purifying an individual blood component or limited number of components, such as red blood cells, immunoglobulins, serum albumin, or the like, and combining the component or components ex vivo with the chemically reactive modified peptides. The functionalized blood or blood component may then be returned to the host to provide in vivo the subject therapeutically effective conjugates. The blood also may be treated to prevent coagulation during handling ex vivo. Other sources of blood components, such as recombinant proteins are also suitable for the preparation of the conjugates of the present invention.

Some of the preferred compounds of the invention are derivatives of $PYY_{1-36}$ and $PYY_{3-36}$. These derivatives comprise a strategically placed maleimido-containing group as described above. $PYY_{1-36}$ and $PYY_{3-36}$ have the following structures:

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|
| PYY | | | | | | | | | | | | | | | | | | | | | | | | | | | | | | | | | | | |
| Y | P | I | K | P | E | A | P | G | E | D | A | S | P | E | E | L | N | R | Y | Y | A | S | L | R | H | Y | L | N | L | V | T | R | Q | R | Y* |
| | | I | K | P | E | A | P | G | E | D | A | S | P | E | E | L | N | R | Y | Y | A | S | L | R | H | Y | L | N | L | V | T | R | Q | R | Y** |

*SEQ ID NO: 3
**SEQ ID NO: 4

These peptides have an alpha helical structure starting at position 18 running through to position 36 (example on PYY in Biochemistry, 2000, 39, 9935). The amino acids at positions 22, 25, 29 and 33 can be considered as relatively important for the activity. All derivatives of these peptides can be truncated, modified, mutated or intact peptides. Preferably, they are able to expose side chains found on these four amino acid residues. These residues are conserved in $PYY_{1-36}$ (SEQ ID NO: 3), $PYY_{3-36}$ (SEQ ID NO: 4), pancreatic polypeptide and neuropeptide Y. Secondary conserved amino acids of potential importance can be those at positions 5, 8, 9, 12, 15, 20, 24, 27, 32, 35 and 36.

Another aspect of the invention is to reduce excess intestinal water and decreasing excess electrolyte secretion.

Another aspect of the invention is to relieve tumor necrosis factor (TNF)-induced acute pancreatitis through the inhibition of NF-B translocation to acinar nuclei (Vona-Davis L. et al., *J. Am. Coll. Surg.*, 2004, 199, 87-95) using the DAC $PYY_{1-36}$ series of derivatives.

BRIEF DESCRIPTION OF DRAWINGS

Further features and advantages of the invention will become more readily apparent from the following description of preferred embodiments as illustrated by way of examples in the appended drawings wherein:

FIG. 1 is a diagram showing a comparison between the anti-obesity activity of $PYY_{3-36}$ and the anti-obesity activity a compound according to a preferred embodiment of the invention, wherein the anti-obesity activity of these compounds has been determined in an experiment by administering them, at various doses, to Sprague-Dawley rats and by measuring the food consumption of these rats before and after administration of these compounds;

FIG. 2 is another diagram as in FIG. 1, wherein the PYY peptide and the compound according to a preferred embodiment of the invention have been administered to the rats according to other dosages;

FIG. 3 is a diagram showing the reduction in food intake after 24 hours, which has been generated by the administration of the PYY peptide and the compound of the invention, during the experiment described in FIG. 1;

FIG. 4 is a diagram showing the reduction in food intake after 24 hours, which has been generated by the administration of the PYY peptide and the compound of the invention, during the experiment described in FIG. 2.

DESCRIPTION OF PREFERRED EMBODIMENTS

Figure 5:
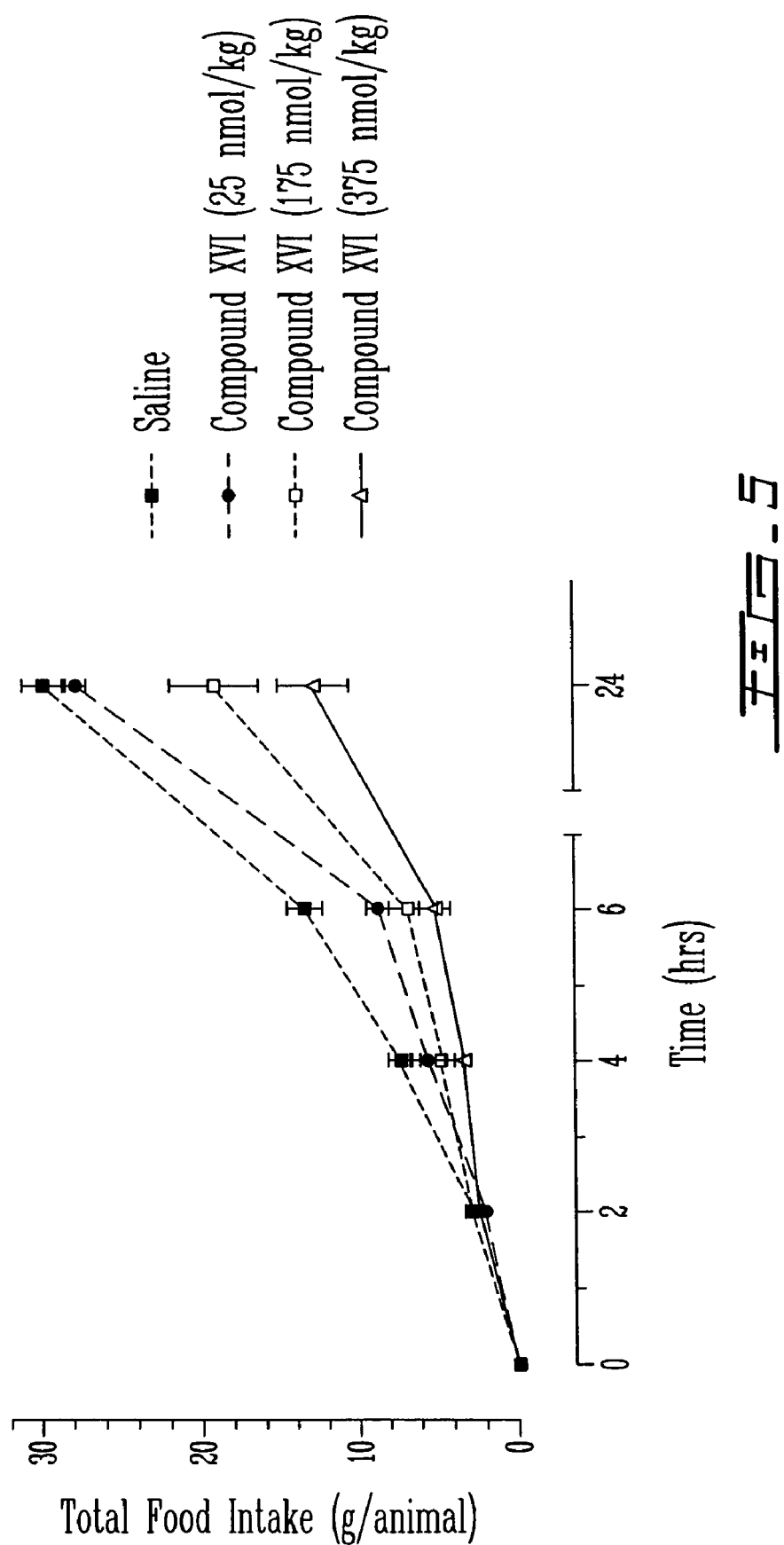
FIG. 5 is a plot showing the influence of the dosage of another compound according to a preferred embodiment of the invention on the total food intake of Sprague-Dawley rats over time.

The following non-limiting examples further illustrate the invention.

EXAMPLES

1. Synthetic Scheme

General

The synthesis of the PYY peptides and functional derivatives thereof was performed using an automated solid-phase procedure on a Symphony Peptide Synthesizer with manual intervention during the generation of the DAC peptide. The synthesis was performed on Fmoc-protected Ramage amide linker resin, using Fmoc-protected amino acids. Coupling was achieved by using O-benzotriazol-1-yl-N,N,N',N'-tetramethyl-uronium hexafluorophosphate (HBTU) and diisopropylethylamine (DIEA) as the activator cocktail in N,N-dimethylformamide (DMF) solution. The Fmoc protective group was removed using 20% piperidine/DMF. When needed, a Boc-protected amino acid was used at the N-terminus in order to generate the free $N_\alpha$-terminus after the peptide was cleaved from resin. All amino acids used during the synthesis possessed the L-stereochemistry unless otherwise stated. Sigmacoted glass reaction vessels were used during the synthesis.

Compound I ($PYY_{3-36}$)

```
Ile-Lys-Pro-Glu-Ala-Pro-Gly-Glu-Asp-  (SEQ ID NO: 4)
Ala-Ser-Pro-Glu-Glu-Leu-Asn-Arg-Tyr-
Tyr-Ala-Ser-Leu-Arg-His-Tyr-Leu-Asn-
Leu-Val-Thr-Arg-Gln-Arg-Tyr-CONH₂
```

Step 1: Solid phase peptide synthesis of the DAC™ peptide on a 100 μmole scale was performed using manual and automated solid-phase synthesis, a Symphony Peptide Synthesizer and Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Glu(tBu)-OH, Fmoc-Glu(tBu)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH. They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The peptide was cleaved from the resin using 85% TFA/5% TIS/5% thioanisole and 5% phenol, followed by precipitation by dry-ice cold (0-4° C.) Et$_2$O. The crude peptide was collected on a polypropylene sintered funnel, dried, redissolved in a 40% mixture of acetonitrile in water (0.1% TFA) and lyophilized to generate the corresponding crude material used in the purification process.

Compound II

Ile-Lys-Pro-Glu-Ala-Pro-Gly-Glu-Asp- (SEQ ID NO: 5)

Ala-Ser-Pro-Glu-Glu-Leu-Asn-Arg-Tyr-

Tyr-Ala-Ser-Leu-Arg-His-Tyr-Leu-Asn-

Leu-Val-Thr-Arg-Gln-Arg-Tyr-

Lys(MPA)-CONH$_2$

Step 1: Solid phase peptide synthesis of the DAC derivative on a 100 μmole scale was performed using manual solid-phase synthesis, a Symphony Peptide Synthesizer and Fmoc protected Ramage resin. The following protected amino acids were sequentially added to resin: Fmoc-Lys(Aloc)-OH, Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Glu(tBu)-OH, Fmoc-Glu(tBu)-OH, Fmoc-Pro-OH, Fmoc-Ser(tBu)-OH, Fmoc-Glu(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH. The following protected amino acids were sequentially added to resin. They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold (0-4° C.) Et$_2$O (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound III

MPA-Ile-Lys-Pro-Glu-Ala-Pro-Gly-Glu- (SEQ ID NO: 16)

Asp-Ala-Ser-Pro-Glu-Glu-Leu-Asn-Arg-

Tyr-Tyr-Ala-Ser-Leu-Arg-His-Tyr-Leu-

Asn-Leu-Val-Thr-Arg-Gln-Arg-Tyr-

CONH$_2$

Step 1: Solid phase peptide synthesis of the DAC derivative on a 100 μmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Glu(tBu)-OH, Fmoc-Glu(tBu)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Fmoc-Ile-OH MPA-OH. They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The peptide was cleaved from the resin using 85% TFA/5% TIS/5% thioanisole and 5% phenol, followed by precipitation by dry-ice cold (0-4° C.) Et$_2$O (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound IV

Ile-Lys-Pro-Glu-Ala-Pro-Gly-Glu-Asp- (SEQ ID NO: 6)

Ala-Ser-Pro-Glu-Glu-Leu-Asn-Arg-Tyr-

Tyr-Ala-Ser-Lys(MPA)-Arg-His-Tyr-

Leu-Asn-Leu-Val-Thr-Arg-Gln-Arg-Tyr-

CONH$_2$

Step 1: Solid phase peptide synthesis of the DAC derivative on a 100 μmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Lys(Aloc)-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Glu(tBu)-OH, Fmoc-Glu(tBu)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH. They were dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et$_2$O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound V

Ile-Lys-Pro-Glu-Ala-Pro-Gly-Glu-Asp- (SEQ ID NO: 7)

Ala-Ser-Pro-Glu-Glu-Leu-Asn-Arg-

Lys(MPA)-Tyr-Ala-Ser-Leu-Arg-His-

Tyr-Leu-Asn-Leu-Val-Thr-Arg-Gln-Arg-

Tyr-CONH$_2$

Step 1: Solid phase peptide synthesis of the DAC derivative on a 100 µmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Lys(Aloc)-OH, Fmoc-Arg(Pbf)-OH, Fmoc-Asn(Trt)-OH, Fmoc-Leu-OH, Fmoc-Glu(tBu)-OH, Fmoc-Glu(tBu)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et$_2$O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound VI

Ile-Lys-Pro-Glu-Ala-Pro-Gly-Glu-Asp- (SEQ ID NO: 8)

Ala-Ser-Pro-Glu-Glu-Lys(MPA)-Asn-

Arg-Tyr-Tyr-Ala-Ser-Leu-Arg-His-Tyr-

Leu-Asn-Leu-Val-Thr-Arg-Gln-Arg-Tyr-

CONH$_2$

Step 1: Solid phase peptide synthesis of the DAC derivative on a 100 µmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Al a-OH, Fmoc-Tyr(tBu)-OH, Fmoc-Tyr(tBu)-OH, Fmoc-Arg(Pbf)-OH, Fmoc-Asn(Trt)-OH, Fmoc-Lys(Aloc)-OH, Fmoc-Glu(tBu)-OH, Fmoc-Glu(tBu)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH They were dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et$_2$O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound VII

Ile-Lys-Pro-Glu-Ala-Pro-Gly-Glu-Asp- (SEQ ID NO: 9)

Ala-Ser-Pro-Glu-Lys(MPA)-Leu-Asn-

```
-continued
Arg-Tyr-Tyr-Ala-Ser-Leu-Arg-His-Tyr-

Leu-Asn-Leu-Val-Thr-Arg-Gln-Arg-Tyr-

CONH₂
```

Step 1: Solid phase peptide synthesis of the DAC derivative on a 100 μmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Lys(Aloc)-OH, Fmoc-Glu(tBu)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH They were dissolved in N,N-dimethylformamide (DMF) and, according to the sequence, activated using O-benzotriazol-1-yl-N, N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh₃)₄ dissolved in 5 mL of C₆H₆:CHCl₃ (1:1): 2.5% NMM (v:v): 5% AcOH (v:v) for 2 h (Step 2). The resin is then washed with CHCl₃ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et₂O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound VIII

```
Ile-Lys-Pro-Glu-Ala-Pro-Gly-Glu-      (SEQ ID NO: 10)

Asp-Ala-Ser-Pro-Lys(MPA)-Glu-Leu-

Asn-Arg-Tyr-Tyr-Ala-Ser-Leu-Arg-

His-Tyr-Leu-Asn-Leu-Val-Thr-Arg-

Gln-Arg-Tyr-CONH₂
```

Step 1: Solid phase peptide synthesis of the DAC derivative on a 100 μmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Glu(tBu)-OH, Fmoc-Lys(Aloc)-OH, Fmoc-Pro-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh₃)₄ dissolved in 5 mL of C₆H₆:CHCl₃ (1:1): 2.5% NMM (v:v): 5% AcOH (v:v) for 2 h (Step 2). The resin is then washed with CHCl₃ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et₂O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound IX

```
Ile-Lys-Pro-Glu-Ala-Pro-Gly-Glu-      (SEQ ID NO: 11)

Asp-Ala-Ser-Lys(MPA)-Glu-Glu-Leu-

Asn-Arg-Tyr-Tyr-Ala-Ser-Leu-Arg-

His-Tyr-Leu-Asn-Leu-Val-Thr-Arg-

Gln-Arg-Tyr-CONH₂
```

Step 1: Solid phase peptide synthesis of the DAC derivative on a 100 μmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Fmoc-Tyr(tBu)-OH, Fmoc-Tyr(tBu)-OH, Fmoc-Arg(Pbf)-OH, Fmoc-Asn(Trt)-OH, Fmoc-Leu-OH, Fmoc-Glu(tBu)-OH, Fmoc-Glu(tBu)-OH, Fmoc-Lys(Aloc)-OH, Fmoc-Ser(tBu)-OH, Fmoc-Ala-OH, Fmoc-Asp(tBu)-OH, Fmoc-Glu(tBu)-OH, Fmoc-Gly-OH, Fmoc-Pro-OH, Fmoc-Ala-OH, Fmoc-Glu(tBu)-OH, Fmoc-Pro-OH, Fmoc-Lys(Boc)-OH, Boc-Ile-OH They were dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et$_2$O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound X

Ac-Ala-Ser-Leu-Arg-His-Tyr-Leu-    (SEQ ID NO: 12)
Asn-Leu-Val-Thr-Arg-Gln-Arg-Tyr-
CONH$_2$

Step 1: Solid phase peptide synthesis of the DAC derivative on a 100 µmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Acetic Acid. They were dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The peptide was cleaved from the resin using 85% TFA/5% TIS/5% thioanisole and 5% phenol, followed by precipitation by dry-ice cold Et$_2$O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound XI

MPA-Ala-Ser-Leu-Arg-His-Tyr-Leu-    (SEQ ID NO: 12)
Asn-Leu-Val-Thr-Arg-Gln-Arg-Tyr-
CONH$_2$

Step 1: Solid phase peptide synthesis of the DAC derivative on a 100 µmole scale was performed using manual solid-phase synthesis, a Symphony Peptide Synthesizer and Fmoc protected Ramage resin. The following protected amino acids were sequentially added to resin: Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, MPA-OH. They were dissolved in N,N-dimethylformamide (DMF) and, according to the sequence, activated using O-benzotriazol-1-yl-N,N,N', N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The peptide was cleaved from the resin using 85% TFA/5% TIS/5% thioanisole and 5% phenol, followed by precipitation by dry-ice cold Et$_2$O (0-4° C.) (Step 4). The crude peptide was collected on a polypropylene sintered funnel, dried, redissolved in a 40% mixture of acetonitrile in water (0.1% TFA) and lyophilized to generate the corresponding crude material used in the purification process.

Compound XII

Ac-Ala-Ser-Leu-Arg-His-Tyr-Leu-    (SEQ ID NO: 13)
Asn-Leu-Val-Thr-Arg-Gln-Arg-Tyr-
Lys(MPA)-CONH$_2$

Step 1: Solid phase peptide synthesis of the DAC derivative on a 100 µmole scale was performed using manual solid-phase synthesis, a Symphony Peptide Synthesizer and Fmoc protected Ramage resin. The following protected amino acids were sequentially added to resin: Fmoc-Lys(Aloc)-OH, Fmoc-Tyr(tBu)-OH, Fmoc-Arg(Pbf)-OH, Fmoc-Gln(Trt)-OH, Fmoc-Arg(Pbf)-OH, Fmoc-Thr(tBu)-OH, Fmoc-Val-OH, Fmoc-Leu-OH, Fmoc-Asn(Trt)-OH, Fmoc-Leu-OH, Fmoc-Tyr(tBu)-OH, Fmoc-His(Trt)-OH, Fmoc-Arg(Pbf)-OH, Fmoc-Leu-OH, Fmoc-Ser(tBu)-OH, Fmoc-Ala-OH, Acetic Acid. They were dissolved in N,N-dimethylformamide (DMF) and, according to the sequence, activated using O-benzotriazol-1-yl-N,N,N',N'-tetramethyl-uronium hexafluorophosphate (HBTU) and Diisopropylethylamine (DIEA). Removal of the Fmoc protecting group was achieved using a solution of 20% (V/V) piperidine in N,N-dimethylformamide (DMF) for 20 minutes (step 1).

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (Step 3). Between every coupling, the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et$_2$O (0-4° C.)

2. Purification procedure:

Each product was purified by preparative reversed phase HPLC, using a Varian (Dynamax) preparative binary HPLC system.

Purification of all the above compounds were performed using a Phenomenex Luna 10µ phenyl-hexyl, 50 mm×250 mm column (particules 10µ) equilibrated with a water/TFA mixture (0.1% TFA in H$_2$O; Solvent A) and acetonitrile/TFA (0.1% TFA in CH$_3$CN; Solvent B). Elution was achieved at 50 mL/min by running various gradients of % B gradient over 180 min. Fractions containing peptide were detected by UV absorbance (Varian Dynamax UVD II) at 214 and 254 nm.

Fractions were collected in 25 mL aliquots. Fractions containing the desired product were identified by mass detection after direct injection onto LC/MS. The selected fractions were subsequently analyzed by analytical HPLC (20-60% B over 20 min; Phenomenex Luna 5μ phenyl-hexyl, 10 mm×250 mm column, 0.5 mL/min) to identify fractions with ≧90% purity for pooling. The pool was freeze-dried using liquid nitrogen and subsequently lyophilized for at least 2 days to yield a white powder.

Other suitable peptides are represented in the following sequences:

```
Tyr-Pro-Ala-Lys-Pro-Glu-Ala-Pro-    (SEQ ID NO: 14)

Gly-Glu-Asp-Ala-Ser-Pro-Glu-Glu-

Leu-Ser-Arg-Tyr-Tyr-Ala-Ser-Leu-

Arg-His-Tyr-Leu-Asn-Leu-Val-Thr-

Arg-Gln-Arg-Tyr; and

Tyr-Pro-Ile-Lys-Pro-Glu-Ala-Pro-    (SEQ ID NO: 15)

Gly-Glu-Asp-Ala-Ser-Pro-Glu-Glu-

Leu-Asn-Arg-Tyr-Tyr-Ala-Ser-Leu-

Arg-His-Tyr-Leu-Asn-Leu-Leu-Thr-

Arg-Pro-Arg-Tyr.
```

3. Table of Products

TABLE 1

List of the various peptides prepared together with their molecular weight

| Compound no: | Theoretical M.W. | Actual M.W. |
|---|---|---|
| I | 4049.5 | 4049.5 |
| II | 4328.8 | 4328.6 |
| III | 4200.6 | 4200.0 |
| IV | 4255.5 | 4257.1 |
| V | 4212.2 | 4214.1 |
| VI | 4197.2 | 4199.0 |
| VII | 4229.1 | 4231.5 |
| VIII | 4239.2 | 4241.6 |
| IX | 4255.2 | 4257.5 |
| X | 1931.2 | 1930.7 |
| XI | 2185.5 | 2185.0 |
| XII | 2210.5 | 2210.1 |

4. Flow Diagram for Each Compound:

A) Identical synthetic schemes, as exemplified in the flow diagram below, were employed for all stabilized DAC™. Of course, for the natives the Aloc removal step along with the addition step of AEEA and\or MPA were omitted.

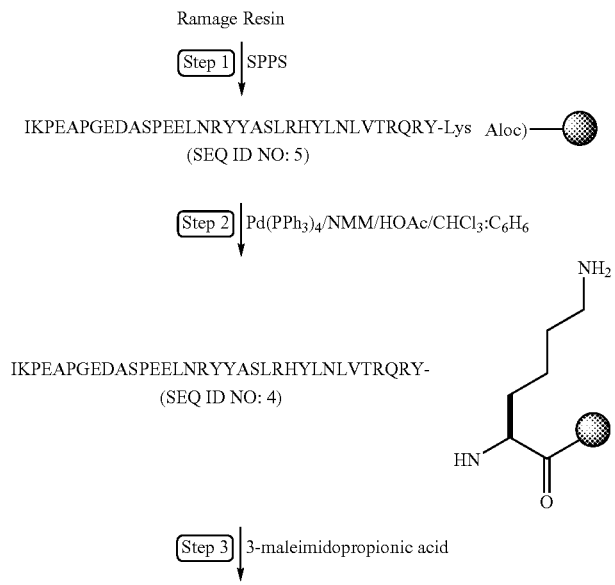

Ramage Resin

Step 1 | SPPS

IKPEAPGEDASPEELNRYYASLRHYLNLVTRQRY-Lys Aloc)—
(SEQ ID NO: 5)

Step 2 | Pd(PPh$_3$)$_4$/NMM/HOAc/CHCl$_3$:C$_6$H$_6$

IKPEAPGEDASPEELNRYYASLRHYLNLVTRQRY-
(SEQ ID NO: 4)

Step 3 | 3-maleimidopropionic acid

-continued

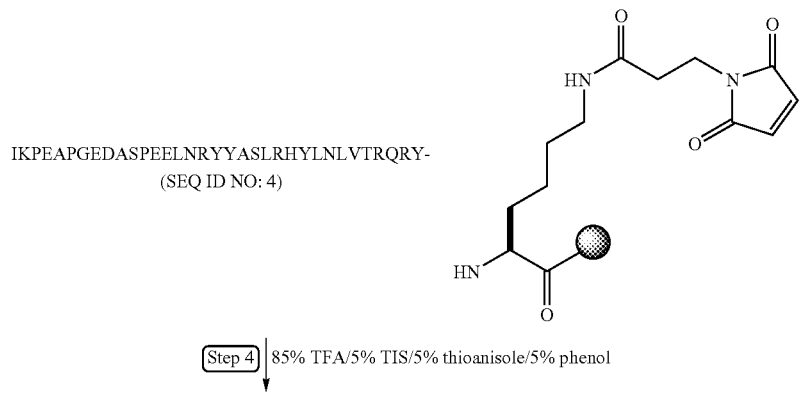

IKPEAPGEDASPEELNRYYASLRHYLNLVTRQRY-
(SEQ ID NO: 4)

Step 4 | 85% TFA/5% TIS/5% thioanisole/5% phenol

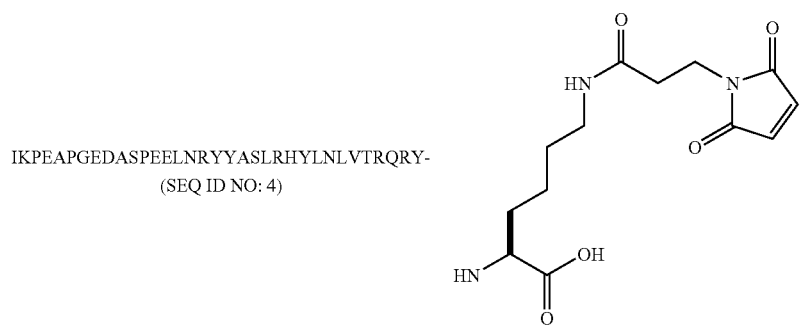

IKPEAPGEDASPEELNRYYASLRHYLNLVTRQRY-
(SEQ ID NO: 4)

Direct Synthesis

Alternative Synthesis of Compound III and Isolation of Compound XIII $PYY_{3-36}$ (human) is a 34 amino acids peptide. From the sequence the N-terminal and lysine residue (in position 2) can be modified by direct attachment of the DAC group. Since the peptide is not very soluble in DMF, it has to be treated with TFA to be dissolved and then neutralized by NMM. Thus the reaction has to be in the TFA/NMM buffer system. However, both amino groups in N-terminal and lysine show the same reactivity towards MPA-OSu under the buffer system. With 1 equivalent of MPA-OSu in the TFA/NMM system, the reaction produced four different products. The differences between these products are the position of the MPA on the sequence and the number of MPA attached to the sequence. Two positional isomers of having a single MPA group (MPA-PYY) have been obtained as major products and two positional isomers having two MPA groups ((MPA)$_2$-PYY and cyclization)) have been minor products. These four products were separated by HPLC. The positional isomers bearing a single MPA have been isolated to give MPA-PYY positional isomer-1 (Compound XIII) and positional isomer-2 (Compound III) in 27.8 and 15.2% yield respectively (see the following scheme). The starting material PYY was also recovered (37.6% recovery).

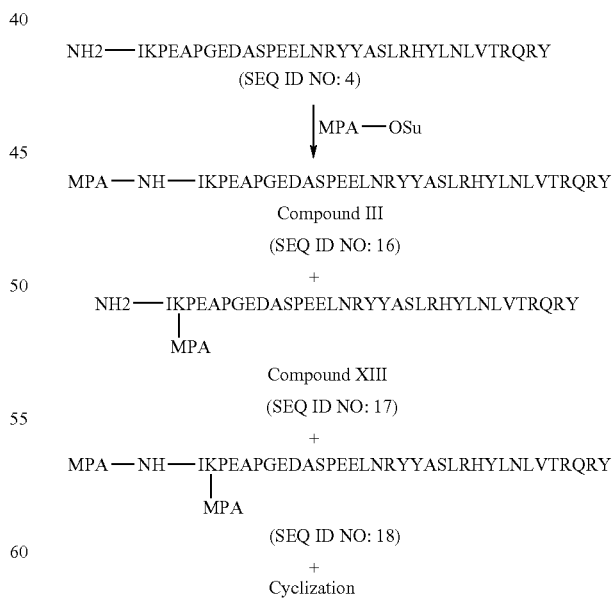

Compounds XIV and XV

In the same way, PYY can react with excess MPA-OA-OpNP for overnight to give two positional isomers having a single MPA group: MPA-OA-PYY isomer-1 (Compound XIV, 19% yield) and MPA-OA-PYY isomer-2 (Compound XV, 17.2% yield). In this case, MPA-OA-OpNP ester is less reactive and thus a large excess reagent is required for the reaction to occur. The minor products are still cyclization and (MPA-OA)$_2$-PYY.

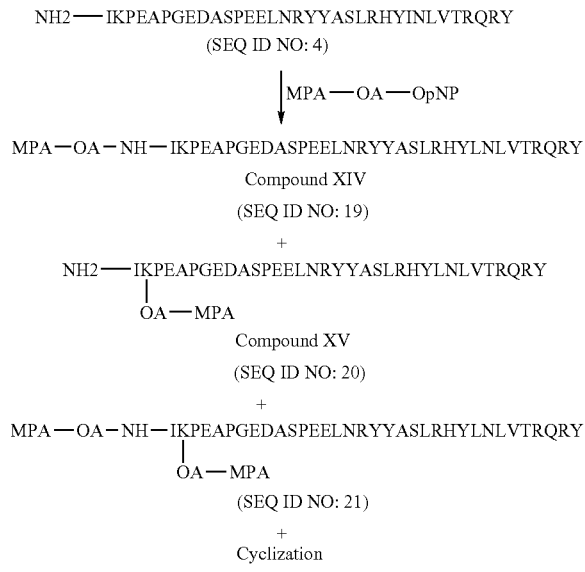

PYY (100 mg) was dissolved in DMF (5 mL) in the presence of TFA (25 µL) with the help of sonication. Then NMM (100 µL) was added followed by addition of MPA-OSu (5.6 mg). The reaction was stirred at room temperature for 2.5 h. The reaction was quenched by addition of AcOH (1 mL). The DMF solution was diluted with water to 20 mL. The products were separated by semi-preparative HPLC column (3 injections) to give PYY (37.6 mg), MPA-PYY isomer-1 (Compound XII, 27.8 mg) and PMA-PYY isomer-2 (Compound XIII, 15.2 mg).

PYY (50 mg) was dissolved in DMF (5 mL) in the presence of TFA (25 µL). NMM (100 µL) was then added followed by MPA-OA-OpNP (50 mg). The reaction was stirred for 16 h at room temperature. The linker was removed by addition of ether and the solution removed after centrifugation. The precipitate was dissolved in water and injected to semi-preparative HPLC to give MPA-OA-PYY isomer-1 (Compound XIV, 9.5 mg) and MPA-OA-PYY isomer-2 (Compound XV, 8.6 mg).

Compound XVI

Compound III was solubilized in nanopure water at a concentration of 10 mM then diluted to 1 mM into a solution of HSA (25%, Cortex-Biochem, San Leandro, Calif.). The sample were then incubated at 37° C. for 30 min. Prior to purification, the conjugate solution was diluted to 5% HSA in 20 mM sodium phosphate buffer (pH 7) composed of 5 mM sodium octanoate and 750 mM (NH$_4$)$_2$SO$_4$.

Using an ÄKTA purifier (Amersham Biosciences, Uppsala, Sweden), the conjugate was loaded at a flow rate of 2.5 ml/min onto a 50 ml column of butyl sepharose 4 fast flow resin (Amersham Biosciences, Uppsala, Sweden) equilibrated in 20 mM sodium phosphate buffer (pH 7) composed of 5 mM sodium octanoate and 750 mM (NH$_4$)$_2$SO$_4$. Under these conditions, Compound XVI adsorbed onto the hydrophobic resin whereas essentially all non-conjugated (unreacted) HSA eluted within the void volume of the column. The conjugate was further purified from any free (unreacted) maleimido PYY$_{3-36}$ derivative by applying a linear gradient of decreasing (NH$_4$)$_2$SO$_4$ concentration (750 to 0 mM) over 4 column volumes. The purified conjugate was then desalted and concentrated using Amicon® ultra centrifugal (30 kDa) filter devices (Millipore Corporation, Bedford, Mass.). Finally, the conjugate solution was immersed into liquid nitrogen, lyophilized and stored at −80° C.

Compounds XVII to XXII

Compounds XVII to XXII are all conjugates having in form of a white solid and they have been prepared according to the same manner than Compound XVI. The table below indicates from which peptides these conjugates have been prepared. Moreover, the molecular weight of each conjugate is given.

TABLE 2

Conjugates obtained from various peptides.

| Peptides | Conjugate | M$_r$(conjugates) | |
|----------|-----------|------------|----------|
|          |           | Predicted  | Measured |
| Compound III  | Compound XVI    | 70643 | 70639 |
| Compound XIII | Compound XXI    | 70645 | 70640 |
| Compound XI   | Compound XXII   | 68629 | 68626 |
| Compound II   | Compound XIX    | 70771 | 70668 |
| Compound XII  | Compound XVIII  | 68654 | 68651 |
| Compound XV   | Compound XVII   | 70787 | 70785 |
| Compound XIV  | Compound XX     | 70787 | 70785 |

Example I

In vitro Binding Assay: Selectivity Toward the NPY Y2 Receptor

Serially diluted test compounds ($10^{-13}$M to $10^{-5}$M) were incubated for 60 minutes at 37° C. in the presence of 4.09 µg of human neuropeptide Y2 receptor expressing human KAN-TS cells and 50000 CPM of $^{125}$I-PYY$_{3-36}$. The individual solutions were filtered (Whatman 934 A/H filters) and washed with ice-cold buffer. The filters were then placed in a gamma counter and the values reported as the percent relative to the maximum gamma emission at the zero concentration as a function of test compound concentration as shown on Table 3.

TABLE 3

Comparison of the NPY Y2 Receptor binding of the PYY derivatives

| Peptide | Sequence | IC$_{50}$(nM) |
|---------|----------|---------------|
| Compound I | PYY$_{3-36}$ | 1.17 |
| NPY$_{(13-36)}$ control | — | 2.48 |
| Compound XVI | N-term SL PYY$_{3-36}$-HSA conjugate | 35.2 |
| Compound XVII | N-term LL PYY$_{3-36}$-HSA conjugate | 52.4 |
| Compound XX | N-K5 LL PYY$_{3-36}$-HSA conjugate | 40.2 |
| Compound XIX | C-term SL PYY$_{3-36}$-HSA conjugate | >10$^3$ |
| Compound XVIII | C-term SL PYY$_{22-36}$-HSA conjugate | >10$^3$ |

Example II

In vitro Binding Assay: Loss of Selectivity Toward the NPY Y1 Receptor

Compound I (PYY$_{3-36}$) and Compound XVI were tested so as to evaluate the preferential binding of the Y2 receptor relative to the Y1 receptor. A selective binding to the Y2 receptor ensures reduced (unwanted) side effects such as for example hypertension.

TABLE 4

Comparison of the NPY Y1 Receptor binding of the PYY derivatives

| Peptide | Sequence | IC$_{50}$(nM) |
|---|---|---|
| Compound I | PYY$_{3-36}$ | 83.2 |
| NPY(human, rat) control | — | 1.09 |
| Compound XVI | N-term SL PYY$_{3-36}$-HSA conjugate | 875.9 |

Example III

Food Intake in Rats Following IV Administration of DAC

Compound I (PYY$_{3-36}$) and Compound III were injected into the tail vein of fully grown Sprague-Dawley rats. Two experiments were carried out so as to verify the influence of the concentration on Compound III of the food consumption of the animal. The food intake was measured pre and post administration (see FIGS. 1 and 2). In experiment 1 on FIG. 1, 4-500 g rats were used and in experiment 2 on FIG. 2, 2-300 g rats were used.

As it can be seen from FIGS. 1 and 2, the results shown a significant reduction in food intake over the 0-12 hour and 12-24 hour periods. The overall effect is very significant over the 0-24 hour period at the highest dose tested (375 nM/kg).

A comparison of reduction in food intake in the two experiments can easily be made by using FIGS. 3 and 4. It can be seen from FIGS. 3 and 4 that PYY$_{3-36}$ does not show reduction in food after 24 hrs at a dose of 25 nmol/kg or at a dose of 375 nmol/kg, while Compound III, at a dose of 375 nmol/kg, shows a strong effect by reducing food intake by 50% after 24 hrs. This comparison demonstrates the long lasting effect of Compound III as compared to the free peptide PYY$_{3-36}$ in vivo.

Example IV

Peripheral vs. Central Action of Compound III

A publication by Batterham (*Nature,* 2002, 418, 650-654) demonstrated the strong effect of PYY$_{3-36}$ administration into the arcuate nucleus to rats on overall food intake. The arcuate nucleus does possess a blood brain barrier and therefore no evidence was ever shown in the literature that peripheral neuropeptide Y2 receptors would have and influence on food intake. Applicant has shown that Compound XVI cannot cross the blood brain barrier (molecular weight >70 000 Da). It is known that PYY$_{3-36}$ interacts with the Y2 receptor found in the arcuate nucleus of the hypothalamus. This receptor is found behind the blood brain barrier (BBB). Nonaka et al., in an article entitled "Characterization of blood-brain barrier permeability to PYY$_{3-36}$ in the mouse" and published in *J. Pharmacol. Exp. Ther.* 2003, 306, 948-53, have hypothesized that the PYY must "cross the BBB" in order to be responsible for the appetite regulating activity.

The injection of Compound XVI i.p. into acclimatized Sprague-Dawley rats in a repeat of the Batterham experiment showed the results shown in FIG. 5.

According to FIG. 5, the 375 nmol/kg dose showed significant reduction in food intake at the 4 hour time point in the experiment. The results are comparable to PYY3-36 25 nmol/kg. Even though there is 15 fold more Compound XVI, pharmacokinetics of absorption will play a role in this head to head comparison. Compound XVI will peak in plasma at a later time than the short peptide. This experiment was done to compare the HSA conjugate directly to the peptide.

It has thus been demonstrated from FIGS. 3 and 4 that the compounds of the invention are very effective for treating food disorders such as obesity. In fact the peptide (Compound III) demonstrated an activity which clearly superior than the activity of PYY$_{3-36}$. It can also be inferred from the results shown in FIG. 5 that the conjugate (Compound XVI) is prevented from crossing the blood brain barrier. In fact reduction in food intake via the PYY receptors (Y1 and Y2, which are thought to have an important role in appetite reduction) is thought to be found on the arcuate nucleus. There is a blood brain barrier separating the arcuate nucleus from plasma. The importance of this experiment is that the conjugate (Compound XVI) has a molecular mass >70 kDA. Therefore, this compound does not cross the blood brain barrier. It can thus be assumed that the PYY receptors involved in the reduction of food intake are found peripherally.

As demonstrated in Kratz et al. *J. Med. Chem.* 2002, 45, 5523-33, when a compound containing a reactive maleimide group such as compound III is injected in a patient, this compound will be eventually covalently bonded to albumin, thereby being converted into Compound XVI. It can thus be said from FIGS. 1 to 5 that the enhanced activity of Compound III with respect to the activity of PYY$_{3-36}$ is due to the fact that Compound III is prevented from crossing the blood brain barrier when the latter is covalently bonded to HSA (converted into Compound XVI).

It has thus been surprisingly noted that by preventing a PYY peptides or derivative thereof from crossing the blood brain barrier, an enhanced anti-obesity activity of this peptide is observed as compared to the peptide alone.

The invention claimed is:

1. A compound comprising a peptide moiety and a Michael acceptor (MA) moiety, the MA moiety being capable of reacting with an amino group, a hydroxyl group or a thiol group on a blood protein so as to form a stable covalent bond, therewith, wherein the compound is of the formula:

$X_1$-$X_2$ Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg $X_3$ (SEQ ID NO:22)

wherein $X_1$ is ile, ile(N-MA) or ile(N-linking group-MA);

$X_2$ is lys or lys($N^\varepsilon$-linking group-MA);

$X_3$ is tyr or a tyr derivative of formula

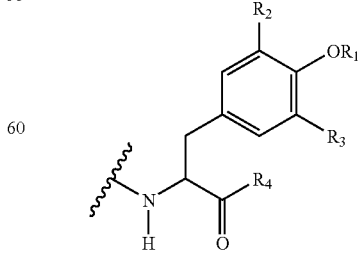

where
R₁ is H, a protecting group (PG), a $C_1$-$C_{10}$ branched, linear or cyclic alkyl, a phosphate or a sulfate;
R₂ and R₃ are same or different and selected from the group consisting of H, D and I; and
R₄ is OH, OPG, OR₅, SH, SPG (sulfur protecting group), SR₅, NH₂, NHPG, N(PG)₂, N(R₅)₂, NR₅PG, or NHR₆, where R₅ is a $C_1$-$C_{10}$ branched, linear or cyclic alkyl, and R₆ is a solid phase support; and wherein
X₁ is ile(N-MA) or ile(N-linking group-MA) when X₂ is lys; and X₂ is lys($N^\epsilon$-linking group-MA) when X₁ is ile.

2. The compound of claim 1, wherein X₁ is ile (N-MA) and X₂ is lys.

3. The compound of claim 1, wherein X₁ is ile (N-linking group-MA) and X₂ is lys.

4. The compound of claim 1, wherein X₁ is ile and X₂ is lys($N^\epsilon$-linking group-MA).

5. The compound of any one of claims 1-4, wherein said Michael acceptor is a maleimido-containing group.

6. The compound of claim 5, wherein said maleimido-containing group is maleimidopropionic acid.

7. The compound of any one of claims 1-4, wherein said blood protein is albumin.

8. The compound of any one of claims 1, 3 and 4, wherein said linking group is selected from the group consisting of (2-amino) ethoxy acetic acid (AEA), ethylenediamine (EDA), amino ethoxy ethoxy succinimic acid (AEES), 2-[2-(2-amino)ethoxy] ethoxy acetic acid (AEEA), AEEA-AEEA, —NH₂—(CH₂)ₙ-COOH where n is an integer from 1 to 20; one or more alkyl chains ($C_1$-$C_{10}$) saturated or unsaturated which optionally comprises oxygen, nitrogen or sulfur atoms motifs, glycine, 3-aminopropionic acid (APA), 8-aminooctanoic acid (OA), 4-aminobenzoic acid (APhA), and combinations thereof.

9. A conjugate formed by the reaction of a compound with a blood protein under conditions sufficient to form a stable covalent bond therewith, wherein the compound comprises a peptide moiety and a Michael acceptor (MA) moiety, wherein the MA moiety is coupled to an amino group, a hydroxyl group or a thiol group on said blood protein, and wherein the compound is of the formula:
X₁-X₂ Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg X₃ (SEQ ID NO:22)
wherein
X₁ is ile, ile(N-MA) or ile(N-linking group-MA);
X₂ is lys or lys($N^\epsilon$-linking group-MA);
X₃ is tyr or a tyr derivative of formula

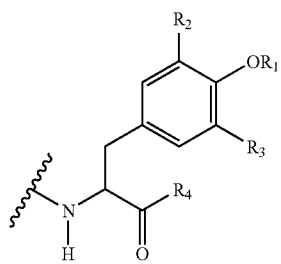

where
R₁ is H, a protecting group (PG), a $C_1$-$C_{10}$ branched, linear or cyclic alkyl, a phosphate or a sulfate;
R₂ and R₃ are same or different and selected from the group consisting of H, D and I; and R₄ is OH, OPG, OR₅, SH, SPG (sulfur protecting group), SR₅, NH₂, NHPG, N(PG)₂, N(R₅)₂, NR₅PG, or NHR₆, where R₅ is a $C_1$-$C_{10}$ branched, linear or cyclic alkyl, and R₆ is a solid phase support;
X₁ is ile(N-MA) or ile(N-linking group-MA) when X₂ is lys; and
X₂ is lys($N^\epsilon$-linking group-MA) when X₁ is ile.

10. The conjugate of claim 9, wherein X₁ is ile(N-MA) and X₂ is lys.

11. The conjugate of claim 9, wherein X₁ is ile(N-linking group-MA) and X₂ is lys.

12. The conjugate of claim 9, wherein X₁ is ile and X₂ is lys($N^\epsilon$-linking group-MA).

13. The conjugate of any one of claims 9-12, wherein said Michael acceptor is a maleimido-containing.

14. The conjugate of claim 13, wherein said maleimido-containing group is maleimidopropionic acid (MPA).

15. The conjugate of any one of claims 9-12, wherein said blood protein is albumin.

16. The conjugate of claim 9, 11, or 12, wherein said linking group is selected from the group consisting of (2-amino) ethoxy acetic acid (AEA), ethylenediamine (EDA), amino ethoxy ethoxy succinimic acid (AEES), 2-[2-(2-amino)ethoxy] ethoxy acetic acid (AEEA), AEEA-AEEA, —NH₂—(CH₂)ₙ—COOH where n is an integer from 1 to 20; one or more alkyl chains ($C_1$-$C_{10}$) saturated or unsaturated which optionally comprises oxygen, nitrogen or sulfur atoms motifs, glycine, 3-aminopropionic acid (APA), 8-aminooctanoic acid (OA), 4-aminobenzoic acid (APhA), and combinations thereof.

17. The compound of any one of claims 1-4 wherein X₃ is tyr-CONH₂.

18. The conjugate of any one of claims 9-12 wherein X₃ is tyr-CONH₂.

19. The conjugate of claim 13, wherein said blood protein is albumin, X₃ is tyr-CONH₂, and said linking group is selected from the group consisting of (2-amino)ethoxy acetic acid (AEA), ethylenediamine (EDA), amino ethoxy ethoxy succinimic acid (AEES), 2-[2-(2-amino)ethoxy] ethoxy acetic acid (AEEA), AEEA-AEEA, —NH₂—(CH₂)ₙ—COOH where n is an integer from 1 to 20; one or more alkyl chains ($C_1$-$C_{10}$) saturated or unsaturated which optionally comprises oxygen, nitrogen or sulfur atoms motifs, glycine, 3-aminopropionic acid (APA), 8-aminooxtanoic acid (OA), 4-aminobenzoic acid (APhA), and combinations thereof.

20. The conjugate of claim 14, wherein said blood protein is albumin, X₃ is tyr-CONH₂, and said linking group is selected from the group consisting of (2-amino)ethoxy acetic acid (AEA), ethylenediamine (EDA), amino ethoxy ethoxy succinimic acid (AEES), 2-[2-(2-amino)ethoxy] ethoxy acetic acid (AEEA), AEEA-AEEA, —NH₂—(CH₂)ₙ—COOH where n is an integer from 1 to 20; one or more alkyl chains ($C_1$-$C_{10}$) saturated or unsaturated which optionally comprises oxygen, nitrogen or sulfur atoms motifs, glycine, 3-aminopropionic acid (APA), 8-aminooxtanoic acid (OA), 4-aminobenzoic acid (APhA), and combinations thereof.

21. The conjugate of claim 10, wherein said blood protein is albumin, X₃ is tyr-CONH₂, and said Michael acceptor is maleimidopropionic acid (MPA).

22. The conjugate of claim 11, wherein said blood protein is albumin, X₃ is tyr-CONH₂, and said Michael acceptor is maleimidopropionic acid (MPA), and said linking group is 8-aminooctanoic acid (OA).

23. The conjugate of claim 12, wherein said blood protein is albumin, X₃ is tyr-CONH₂, said Michael acceptor is maleimidopropionic acid (MPA), and said linking group is 8-aminooxtanoic acid (OA).

24. The compound of claim 6, wherein said blood protein is albumin.

25. The compound of claim 7, wherein said blood protein is albumin.

26. The compound of claim 10, wherein the Michael acceptor is capable of being covalently linked to a thiol group at amino acid residue 34 (Cys34) on albumin.

27. The compound of claim 17, wherein said blood protein is albumin.

28. The compound of claim 6, wherein $X_3$ is tyr-$CONH_2$.

29. The compound of claim 7, wherein $X_3$ is tyr-$CONH_2$.

30. The compound of claim 28, wherein the blood protein is albumin.

31. The compound of claim 29, wherein the blood protein is albumin.

32. The compound of claim 27, wherein the Michael acceptor is capable of being covalently linked to a thiol group at amino acid residue 34 (Cys34) on albumin.

33. The conjugate of claim 13, the blood protein is albumin.

34. The conjugate of claim 14, the blood protein is albumin.

35. The conjugate of claim 15, wherein the Michael acceptor moiety is covalently linked to a thiol group at amino acid residue 34 (Cys34) on albumin.

36. The compound of claim 1, wherein the blood protein is a recombinant protein.

37. The compound of claim 7, wherein the albumin is a recombinant protein.

38. The conjugate of claim 9, wherein the blood protein is a recombinant protein.

39. The conjugate of claim 15, wherein the albumin is a recombinant protein.

* * * * *

UNITED STATES PATENT AND TRADEMARK OFFICE
CERTIFICATE OF CORRECTION

| | | |
|---|---|---|
| PATENT NO. | : 7,601,691 B2 | Page 1 of 1 |
| APPLICATION NO. | : 11/067556 | |
| DATED | : October 13, 2009 | |
| INVENTOR(S) | : Bridon et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 321 days Delete the phrase "by 321 days" and insert -- by 501 days --

Signed and Sealed this

Eighth Day of June, 2010

David J. Kappos
*Director of the United States Patent and Trademark Office*

SEQUENCE LISTING

```
<160> NUMBER OF SEQ ID NOS: 15

<210> SEQ ID NO 1
<211> LENGTH: 37
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: VARIANT
<222> LOCATION: (1)...(1)
<223> OTHER INFORMATION: Xaa is absent, Tyr or Ala
<220> FEATURE:
<221> NAME/KEY: VARIANT
<222> LOCATION: (2)...(2)
<223> OTHER INFORMATION: Xaa is absent or Pro
<220> FEATURE:
<221> NAME/KEY: VARIANT
<222> LOCATION: (3)...(3)
<223> OTHER INFORMATION: Xaa is absent, Lys, Lys analog, Ile, Leu or Ala
<220> FEATURE:
<221> NAME/KEY: VARIANT
<222> LOCATION: (4)...(4)
<223> OTHER INFORMATION: Xaa is absent, Lys, Lys analog or Glu
<220> FEATURE:
<221> NAME/KEY: VARIANT
<222> LOCATION: (5)...(5)
<223> OTHER INFORMATION: Xaa is absent or Pro
<220> FEATURE:
<221> NAME/KEY: VARIANT
<222> LOCATION: (6)...(6)
<223> OTHER INFORMATION: Xaa is is absent, Glu, Val or Asp
<220> FEATURE:
<221> NAME/KEY: VARIANT
<222> LOCATION: (7)...(7)
<223> OTHER INFORMATION: Xaa is absent, Ala, Tyr or Asn
<220> FEATURE:
<221> NAME/KEY: VARIANT
<222> LOCATION: (8)...(8)
<223> OTHER INFORMATION: Xaa is absent or Pro
<220> FEATURE:
<221> NAME/KEY: VARIANT
<222> LOCATION: (9)...(9)
<223> OTHER INFORMATION: Xaa is absent or Gly
<220> FEATURE:
<221> NAME/KEY: VARIANT
<222> LOCATION: (10)...(10)
<223> OTHER INFORMATION: Xaa is absent, Glu or Asp
<220> FEATURE:
<221> NAME/KEY: VARIANT
<222> LOCATION: (11)...(11)
<223> OTHER INFORMATION: Xaa is absent, Asp or Asn
<220> FEATURE:
<221> NAME/KEY: VARIANT
<222> LOCATION: (12)...(12)
<223> OTHER INFORMATION: Xaa is absent, Lys, Lys analog or Ala
<220> FEATURE:
<221> NAME/KEY: VARIANT
<222> LOCATION: (13)...(13)
<223> OTHER INFORMATION: Xaa is is absent, Lys, Lys analog, Ser, Thr or
      Pro
<220> FEATURE:
<221> NAME/KEY: VARIANT
<222> LOCATION: (14)...(14)
<223> OTHER INFORMATION: Xaa is absent, Lys, Lys analog, Ala or Pro
<220> FEATURE:
<221> NAME/KEY: VARIANT
<222> LOCATION: (15)...(15)
<223> OTHER INFORMATION: Xaa is absent, Lys, Lys analog or Glu
<220> FEATURE:
<221> NAME/KEY: VARIANT
<222> LOCATION: (16)...(16)
<223> OTHER INFORMATION: Xaa is absent, Glu, Gln or Asp
<220> FEATURE:
<221> NAME/KEY: VARIANT
<222> LOCATION: (17)...(17)
<223> OTHER INFORMATION: Xaa is absent, Leu or Met
<220> FEATURE:
<221> NAME/KEY: VARIANT
<222> LOCATION: (18)...(18)
<223> OTHER INFORMATION: Xaa is absent, Lys, Lys analog, Ser or Ala
<220> FEATURE:
<221> NAME/KEY: VARIANT
<222> LOCATION: (19)...(19)
<223> OTHER INFORMATION: Xaa is absent, Arg or Gln
<220> FEATURE:
```

<220> FEATURE:
<221> NAME/KEY: VARIANT
<222> LOCATION: (20)...(20)
<223> OTHER INFORMATION: Xaa is absent or Tyr
<220> FEATURE:
<221> NAME/KEY: VARIANT
<222> LOCATION: (21)...(21)
<223> OTHER INFORMATION: Xaa is absent, Tyr or Ala
<220> FEATURE:
<221> NAME/KEY: VARIANT
<222> LOCATION: (22)...(22)
<223> OTHER INFORMATION: Xaa is Ala or Ser
<220> FEATURE:
<221> NAME/KEY: VARIANT
<222> LOCATION: (23)...(23)
<223> OTHER INFORMATION: Xaa is Ser, Asp or Ala
<220> FEATURE:
<221> NAME/KEY: VARIANT
<222> LOCATION: (25)...(25)
<223> OTHER INFORMATION: Xaa is Arg or Lys
<220> FEATURE:
<221> NAME/KEY: VARIANT
<222> LOCATION: (26)...(26)
<223> OTHER INFORMATION: Xaa is His, Arg or Lys
<220> FEATURE:
<221> NAME/KEY: VARIANT
<222> LOCATION: (28)...(28)
<223> OTHER INFORMATION: Xaa is Leu or Ile
<220> FEATURE:
<221> NAME/KEY: VARIANT
<222> LOCATION: (30)...(30)
<223> OTHER INFORMATION: Xaa is Leu or Met
<220> FEATURE:
<221> NAME/KEY: VARIANT
<222> LOCATION: (31)...(31)
<223> OTHER INFORMATION: Xaa is Val, Leu or Ile
<220> FEATURE:
<221> NAME/KEY: VARIANT
<222> LOCATION: (33)...(33)
<223> OTHER INFORMATION: Xaa is Arg or Lys
<220> FEATURE:
<221> NAME/KEY: VARIANT
<222> LOCATION: (34)...(34)
<223> OTHER INFORMATION: Xaa is Gln or Pro
<220> FEATURE:
<221> NAME/KEY: VARIANT
<222> LOCATION: (35)...(35)
<223> OTHER INFORMATION: Xaa is Arg or Lys
<220> FEATURE:
<221> NAME/KEY: VARIANT
<222> LOCATION: (36)...(36)
<223> OTHER INFORMATION: Xaa is Tyr or Tyr derivative
<220> FEATURE:
<221> NAME/KEY: VARIANT
<222> LOCATION: (37)...(37)
<223> OTHER INFORMATION: Xaa is absent, Lys or Lys derivative

<400> SEQUENCE: 1

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Leu Xaa Xaa Tyr Xaa Asn Xaa Xaa Thr
            20                  25                  30

Xaa Xaa Xaa Xaa Xaa
        35

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2, 3, 5, 6, 7, 9, 10, 11
<223> OTHER INFORMATION: Xaa is independantly selected from any natural
    amino acids

```
<400> SEQUENCE: 2

Ala Xaa Xaa Arg Xaa Xaa Xaa Asn Xaa Xaa Xaa Arg
1               5                   10

<210> SEQ ID NO 3
<211> LENGTH: 36
<212> TYPE: PRT
<213> ORGANISM: Homo sapiens

<400> SEQUENCE: 3

Tyr Pro Ile Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 4
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Ile may be linked to a MPA group or a OA-MPA
      group
<220> FEATURE:
<221> NAME/KEY: VARIANT
<222> LOCATION: (2)...(2)
<223> OTHER INFORMATION: Lys may be linked to a MPA group or a OA-MPA
      group
<220> FEATURE:
<221> NAME/KEY: VARIANT
<222> LOCATION: (34)...(34)
<223> OTHER INFORMATION: Tyr may be linked to a resin

<400> SEQUENCE: 4

Ile Lys Pro Glu Ala Pro Gly Glu Asp Ala Ser Pro Glu Glu Leu Ser
1               5                   10                  15

Arg Tyr Tyr Ala Ser Leu Arg His Tyr Leu Asn Leu Val Thr Arg Gln
            20                  25                  30

Arg Tyr

<210> SEQ ID NO 5
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (35)...(35)
<223> OTHER INFORMATION: Lys may be linked to a MPA group or a resin

<400> SEQUENCE: 5

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr Lys
        35
```

```
<210> SEQ ID NO 6
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (22)...(22)
<223> OTHER INFORMATION: Lys is linked to a MPA group

<400> SEQUENCE: 6

Ile Lys Pro Glu Ala Pro Gly Glu Asp Ala Ser Pro Glu Glu Leu Asn
 1               5                  10                  15

Arg Tyr Tyr Ala Ser Lys Arg His Tyr Leu Asn Leu Val Thr Arg Gln
            20                  25                  30

Arg Tyr

<210> SEQ ID NO 7
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (18)...(18)
<223> OTHER INFORMATION: Lys is linked to a MPA group

<400> SEQUENCE: 7

Ile Lys Pro Glu Ala Pro Gly Glu Asp Ala Ser Pro Glu Glu Leu Asn
 1               5                  10                  15

Arg Lys Tyr Ala Ser Leu Arg His Tyr Leu Asn Leu Val Thr Arg Gln
            20                  25                  30

Arg Tyr

<210> SEQ ID NO 8
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (15)...(15)
<223> OTHER INFORMATION: Lys is linked to a MPA group

<400> SEQUENCE: 8

Ile Lys Pro Glu Ala Pro Gly Glu Asp Ala Ser Pro Glu Glu Lys Asn
 1               5                  10                  15

Arg Tyr Tyr Ala Ser Leu Arg His Tyr Leu Asn Leu Val Thr Arg Gln
            20                  25                  30

Arg Tyr

<210> SEQ ID NO 9
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (14)...(14)
<223> OTHER INFORMATION: Lys is linked to a MPA group

<400> SEQUENCE: 9
```

-continued

Ile Lys Pro Glu Ala Pro Gly Glu Asp Ala Ser Pro Glu Lys Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 10
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (13)...(13)
<223> OTHER INFORMATION: Lys is linked to a MPA group

<400> SEQUENCE: 10

Ile Lys Pro Glu Ala Pro Gly Glu Asp Ala Ser Pro Lys Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 11
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (12)...(12)
<223> OTHER INFORMATION: Lys is linked to a MPA group

<400> SEQUENCE: 11

Ile Lys Pro Glu Ala Pro Gly Glu Asp Ala Ser Lys Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Ala may be acetylated or linked to a MPA group

<400> SEQUENCE: 12

Ala Ser Leu Arg His Tyr Leu Asn Leu Val Thr Arg Gln Arg Tyr
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)...(1)

```
-continued

<223> OTHER INFORMATION: Ala is acetylated
<220> FEATURE:
<221> NAME/KEY: VARIANT
<222> LOCATION: (16)...(16)
<223> OTHER INFORMATION: Lys is linked to a MPA group

<400> SEQUENCE: 13

Ala Ser Leu Arg His Tyr Leu Asn Leu Val Thr Arg Gln Arg Tyr Lys
1               5                   10                  15

<210> SEQ ID NO 14
<211> LENGTH: 36
<212> TYPE: PRT
<213> ORGANISM: Artificial Sequence
<220> FEATURE:
<223> OTHER INFORMATION: Synthetic peptide

<400> SEQUENCE: 14

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 15
<211> LENGTH: 36
<212> TYPE: PRT
<213> ORGANISM: Artificial Sequence
<220> FEATURE:
<223> OTHER INFORMATION: Synthetic peptide

<400> SEQUENCE: 15

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Leu Thr
            20                  25                  30

Arg Pro Arg Tyr
        35
```